(12) United States Patent
Moller et al.

(10) Patent No.: US 12,307,581 B2
(45) Date of Patent: May 20, 2025

(54) ELONGATE DEVICE REFERENCES FOR IMAGE-GUIDED PROCEDURES

(71) Applicant: INTUITIVE SURGICAL OPERATIONS, INC., Sunnyvale, CA (US)

(72) Inventors: Zachary F. Moller, San Francisco, CA (US); Leah R. Muller, San Francisco, CA (US); Cynthia Warman, San Carlos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 34 days.

(21) Appl. No.: 17/955,368

(22) Filed: Sep. 28, 2022

(65) Prior Publication Data

US 2023/0099522 A1 Mar. 30, 2023

Related U.S. Application Data

(60) Provisional application No. 63/249,502, filed on Sep. 28, 2021.

(51) Int. Cl.
*G06T 15/20* (2011.01)
*B25J 9/16* (2006.01)
(Continued)

(52) U.S. Cl.
CPC ............ *G06T 15/20* (2013.01); *B25J 9/1689* (2013.01); *G06T 7/70* (2017.01);
(Continued)

(58) Field of Classification Search
CPC .......... B25J 9/1689; G06T 15/20; G06T 7/70; G06T 2207/10068; G06T 2200/24;
(Continued)

(56) References Cited

U.S. PATENT DOCUMENTS 6,380,732 B1 4/2002 Gilboa
6,389,187 B1 5/2002 Greenaway et al.
(Continued)

FOREIGN PATENT DOCUMENTS

| WO | WO-2016191298 A1 | 12/2016 |
| WO | WO-2018005842 A1 | 1/2018 |
| WO | WO-2018005861 A1 | 1/2018 |
| WO | WO-2019245818 A1 | 12/2019 |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Phi Hoang
(74) *Attorney, Agent, or Firm* — Artegis Law Group, LLP

(57) ABSTRACT

System and methods for providing an elongate device reference include a system configured determine a pose, within a workspace, of at least one of a distal portion of an elongate device, or an instrument extendable from the distal portion of the elongate device; acquire a reference pose of the at least one of the distal portion of the elongate device, or the instrument; generate an elongate device reference corresponding to the reference pose; generate an image of the workspace from a perspective associated with the pose; and display, on a display system and on the image of the workspace, the elongate device reference at the reference pose.

20 Claims, 19 Drawing Sheets

(51) Int. Cl.
*G06T 7/70* (2017.01)
*A61B 34/00* (2016.01)
*A61B 34/20* (2016.01)
*A61B 34/30* (2016.01)

(52) U.S. Cl.
CPC ....... *A61B 2034/2059* (2016.02); *A61B 34/25* (2016.02); *A61B 2034/301* (2016.02); *G06T 2200/24* (2013.01); *G06T 2207/10068* (2013.01); *G06T 2210/41* (2013.01)

(58) Field of Classification Search
CPC ..... G06T 2210/41; G06T 19/00; A61B 34/25; A61B 2034/2059; A61B 2034/301; A61B 34/20; A61B 90/361; A61B 2034/107; A61B 2034/105; A61B 34/37; A61B 2034/2061; A61B 2034/2051; G05B 2219/45118
See application file for complete search history.

(56) References Cited

U.S. PATENT DOCUMENTS

| | | | |
|---|---|---|---|
| 7,316,681 | B2 | 1/2008 | Madhani et al. |
| 7,772,541 | B2 | 8/2010 | Froggatt et al. |
| 8,900,131 | B2 | 12/2014 | Chopra et al. |
| 9,259,274 | B2 | 2/2016 | Prisco |
| 9,452,276 | B2 | 9/2016 | Duindam et al. |
| 2006/0013523 | A1 | 1/2006 | Childers et al. |
| 2012/0197619 | A1* | 8/2012 | Namer Yelin ......... G16H 50/50 382/128 |
| 2018/0185104 | A1* | 7/2018 | Olson .................... A61B 34/30 |
| 2019/0365349 | A1* | 12/2019 | Hunter ................ A61B 5/6852 |
| 2020/0030044 | A1 | 1/2020 | Wang et al. |
| 2020/0054399 | A1 | 2/2020 | Duindam et al. |
| 2021/0169605 | A1* | 6/2021 | Calloway ............... A61B 90/36 |
| 2021/0330386 | A1* | 10/2021 | Huysmans ............. A61B 34/10 |
| 2021/0386491 | A1* | 12/2021 | Shmayahu ......... A61B 17/1659 |
| 2022/0061868 | A1* | 3/2022 | Cheon .................... A61B 34/32 |

\* cited by examiner

ELONGATE DEVICE REFERENCES FOR IMAGE-GUIDED PROCEDURES

RELATED APPLICATIONS

This application claims the benefit to U.S. Provisional Application No. 63/249,502, filed Sep. 28, 2021 and entitled "Elongate Device References for Image-guided Procedures," which is incorporated by reference herein.

BACKGROUND

Field of the Various Embodiments

The present disclosure is directed to systems and methods for conducting an image-guided procedure, and more particularly to use of elongate device references for image-guided procedures.

DESCRIPTION OF THE RELATED ART

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions an operator may insert minimally invasive medical instruments (including surgical, diagnostic, therapeutic, or biopsy instruments) to reach a target tissue location. One such minimally invasive technique is to use a flexible and/or steerable elongate device, such as a catheter, that can be inserted into anatomic passageways and navigated toward a region of interest within the patient anatomy. Control of such an elongate device by medical personnel during an image-guided procedure involves the management of several degrees of freedom including at least the management of insertion and retraction of the elongate device as well as steering and/or bend radius of the device. In addition, different modes of operation may also be supported.

Similar image-guided procedures can be found in non-medical contexts as well. For example, an elongate device and/or other instruments could be used to inspect and/or perform operations within pipes, ventilation shafts, passageways, enclosed spaces, and/or the like where direct access by the human operator is not possible or is not practical.

Image guidance features can include images of the patient anatomy and the elongate device obtained from imaging devices located outside of the patient anatomy (e.g., fluoroscopy or X-ray image) and action point markers that can be displayed with the images. However, these features can be difficult to use. For example, images captured from the outside of the patient anatomy may not capture one or more degrees of freedom of the elongate device. Without the image feedback for those degrees of freedom, the operator can have difficulty navigating the elongate device. Similarly, action point markers can be difficult to visualize and to portray with adequate dimensions to aid in navigation. With inadequate dimensional feedback, the operator can have difficulty navigating the elongate device to the action point marker.

Accordingly, it would be advantageous to provide more effective navigation assistance for an elongate device or instrument during an image-guided procedure.

SUMMARY

Consistent with some embodiments, a system includes an elongate device, a display system, one or more processors, and memory storing instructions. When executed by the one or more processors, the instructions cause the one or more processors to determine a pose, within a workspace, of at least one of: a distal portion of the elongate device, or an instrument extendable from the distal portion of the elongate device; acquire a reference pose of the at least one of: the distal portion of the elongate device, or the instrument; generate an elongate device reference corresponding to the reference pose; generate an image of the workspace from a perspective associated with the pose; and display, on the display system and on the image of the workspace, the elongate device reference at the reference pose.

Consistent with some embodiments, an apparatus includes one or more processors, and memory storing instructions. When executed by the one or more processors, the instructions cause the one or more processors to determine a pose, within a workspace, of a distal portion of at least one of an elongate device or an instrument extended beyond the distal portion of the elongate device; acquire a reference pose of the distal portion of at least one of the elongate device or the instrument; generate an elongate device reference corresponding to the reference pose; generate an image of the workspace from a perspective associated with the pose; and output, for display on a display system, the elongate device reference at the reference pose in the image.

Consistent with some embodiments, a method includes determining a pose, within a workspace, of at least one of: a distal portion of an elongate device, or an instrument extendable from the distal portion of the elongate device; acquiring a reference pose of the at least one of: the distal portion of the elongate device, or the instrument; generating an elongate device reference corresponding to the reference pose; generating an image of the workspace from a perspective associated with the pose; and causing to be displayed, on a display system and on the image of the workspace, the elongate device reference at the reference pose.

Consistent with some embodiments, one or more non-transitory machine-readable media include a plurality of machine-readable instructions which when executed by one or more processors are adapted to cause the one or more processors to perform any of the methods described herein.

At least one advantage and technical improvement of the disclosed techniques relative to the prior art is that, with the disclosed techniques, planned and/or saved poses of an elongate device can be shown in three dimensions and/or in multiple degrees of freedom in images of a workspace of interest. Accordingly, an operator of the elongate device can more effectively navigate the elongate device within the workspace to a planned or saved pose. Another advantage and technical improvement is that points of interest can be associated with saved and/or planned poses in 3D and/or in multiple degrees of freedom. Accordingly, the operator can more effectively navigate the elongate device within the workspace to those points of interest. These technical advantages provide one or more technological advancements over prior art approaches.

BRIEF DESCRIPTION OF THE DRAWINGS

So that the manner in which the above recited features of the various embodiments can be understood in detail, a more particular description of the inventive concepts, briefly summarized above, may be had by reference to various embodiments, some of which are illustrated in the appended drawings. It is to be noted, however, that the appended drawings illustrate only typical embodiments of the inventive concepts and are therefore not to be considered limiting of scope in any way, and that there are other equally effective embodiments.

DETAILED DESCRIPTION

Figure 1:
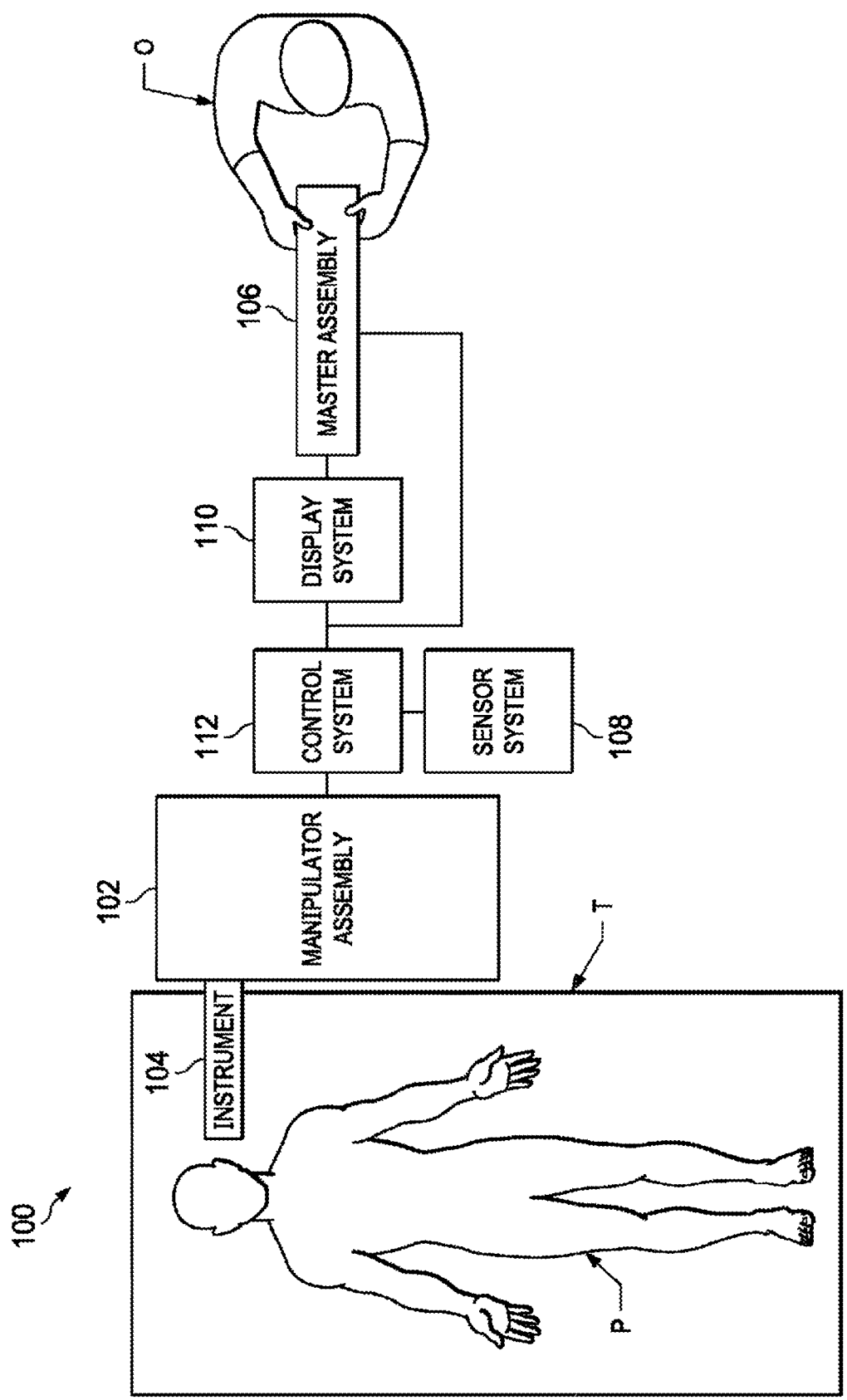
FIG. 1 is a simplified diagram of a teleoperated medical system, according to some embodiments.

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, the terminology in this description is not intended to limit the invention. For example, spatially relative terms—such as "beneath", "below", "lower", "above", "upper", "proximal", "distal", and the like—may be used to describe the relation of one element or feature to another element or feature as illustrated in the figures. These spatially relative terms are intended to encompass different positions and orientations of the elements or their operation in addition to the position and orientation shown in the figures. For example, if the content of one of the figures is turned over, elements described as "below" or "beneath" other elements or features would then be "above" or "over" the other elements or features. Thus, the illustrative term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 1, medical system 100 generally includes a manipulator assembly 102 for operating a medical instrument 104 in performing various procedures on a patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 is mounted to or near an operating table T. A master assembly 106 allows an operator O (e.g., a surgeon, a clinician, or a physician as illustrated in FIG. 1) to view the interventional site and to control manipulator assembly 102.

Master assembly 106 may be located at an operator console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, scroll wheels, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure), and/or one or more servo controlled links (e.g., one more links that may be controlled in response to commands from the control system), and a manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (e.g., dynamically referenced) with the pre-operative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below.

Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), cone-beam computed tomography (CBCT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two-dimensional or three-dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (e.g., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system. For example, PCT Publication WO 2016/191298

(published Dec. 1, 2016) (disclosing "Systems and Methods of Registration for Image Guided Surgery"), which is incorporated by reference herein in its entirety, discloses such one system. Teleoperated medical system 100 may further include optional operations and support systems (not shown) such as illumination systems, steering control systems, irrigation systems, and/or suction systems. In some embodiments, teleoperated medical system 100 may include more than one manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figure 2A:
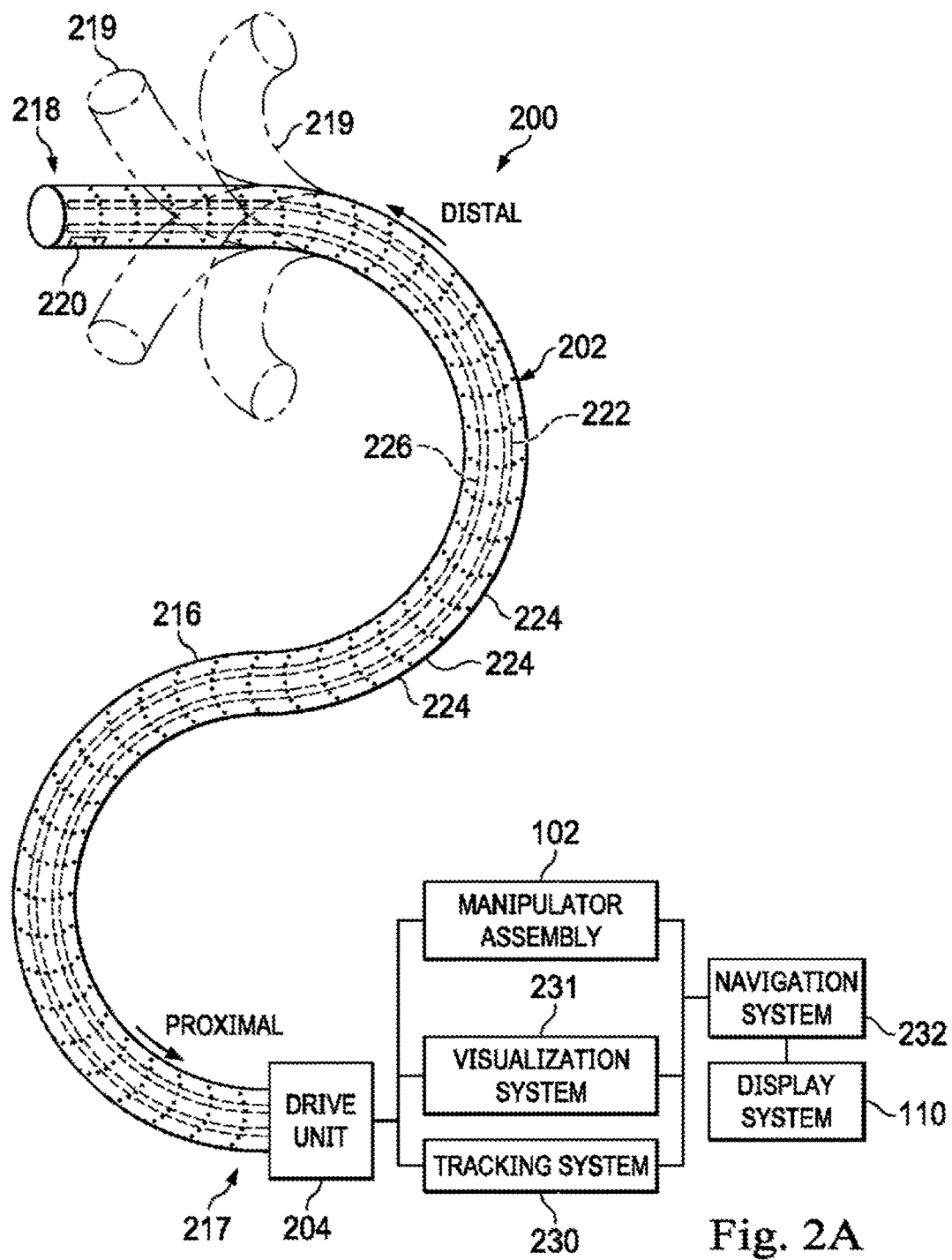
FIG. 2A is a simplified diagram of a medical instrument system, according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (e.g., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and a distal end 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 pm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. Patent Application Publication No. 2006/0013523 (filed Jul. 13, 2005) (disclosing "Fiber optic position and shape sensing device and method relating thereto"); U.S. Pat. No. 7,772,541 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with position sensor system 220 including one or more conductive coils that may be subjected to an externally generated electromagnetic field. Each coil of the EM sensor system then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor system 220 may be positioned along flexible body 216 and then used for shape sensing. In some examples, a history of data from one or more of these sensors taken during a procedure may be used to represent the shape of elongate device 202, particularly if an anatomic passageway is generally static.

Figure 2B:
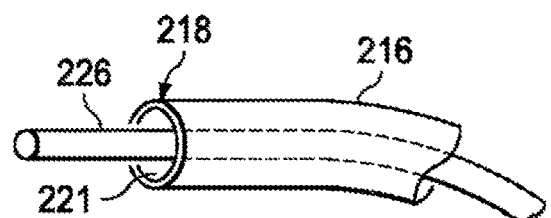
FIG. 2B is a simplified diagram of a medical instrument system with an extended medical instrument, according to some embodiments.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electro surgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216.

In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. Pat. No. 9,259,274 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. Pat. No. 9,452,276 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. Pat. No. 8,900,131, filed May 13, 2011, disclosing "Medical System Providing Dynamic Registration of a Model of an Anatomic Structure for Image-Guided Surgery," and PCT Publication WO 2016/191298, filed May 20, 2016, disclosing "Systems and Methods of Registration for Image Guided Surgery," which are incorporated by reference herein in their entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3A:
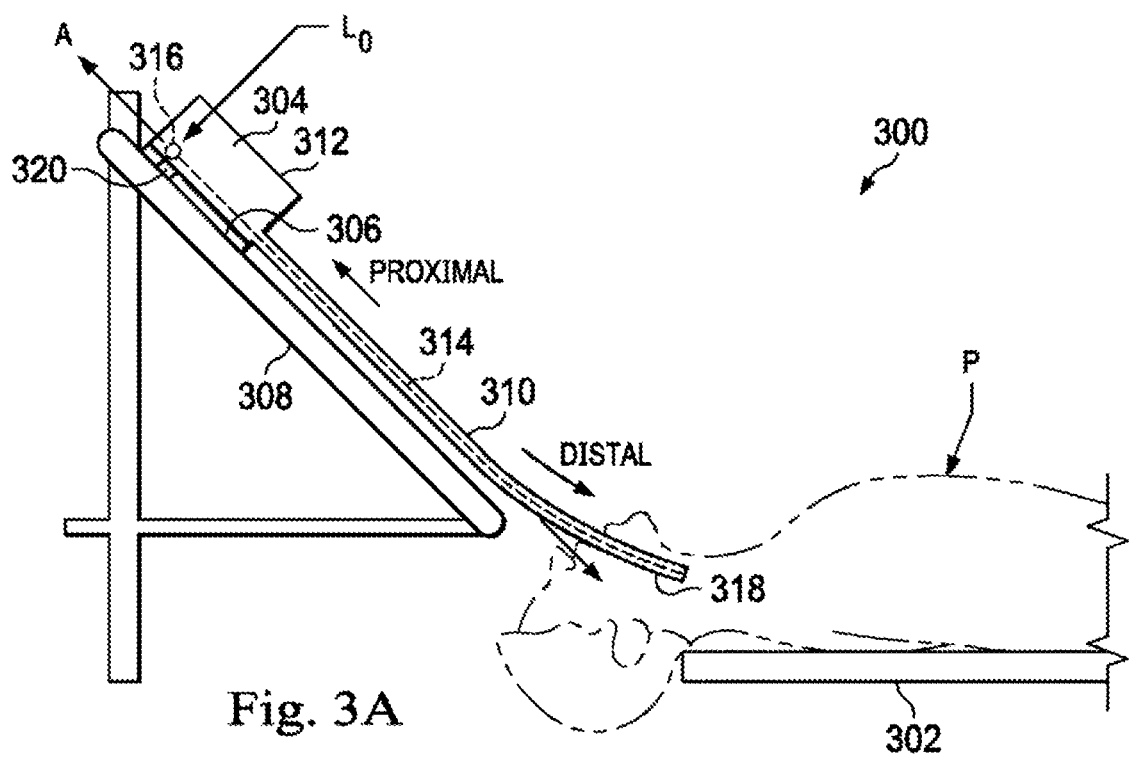
FIGS. 3A and 3B are simplified diagrams of side views of a patient coordinate space including a medical instrument mounted on an insertion assembly, according to some embodiments.
Figure 3B:
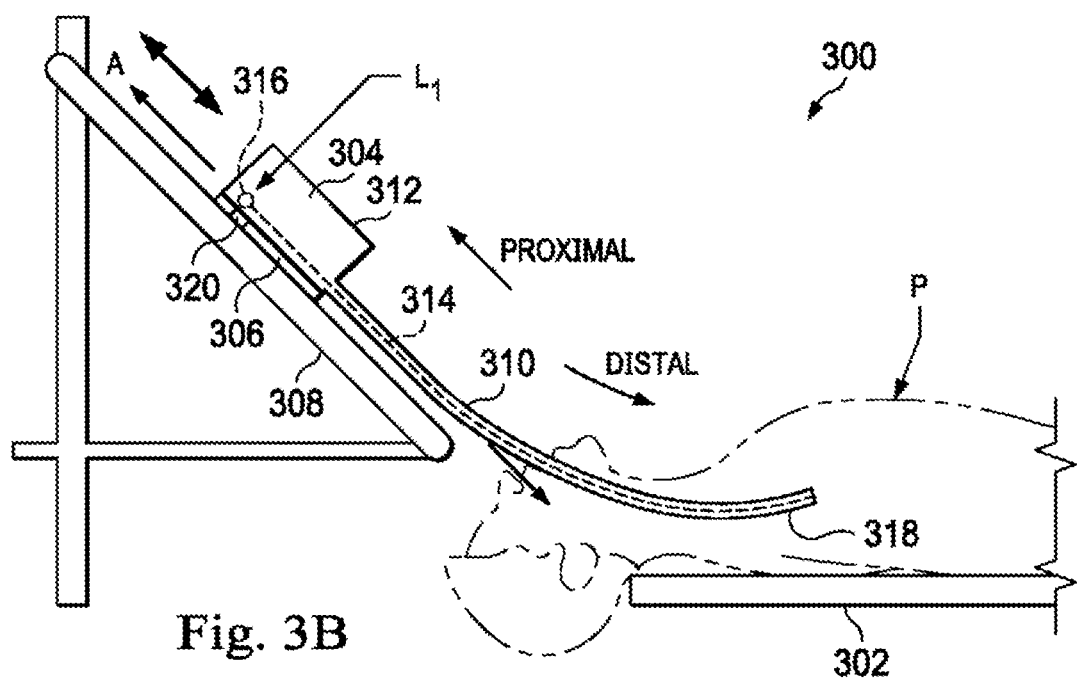

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P that is positioned on the table T of FIG. 1. Patient P may be stationary within the surgical environment in the sense that gross patient movement is limited by sedation, restraint, and/or other means. Cyclic anatomic motion including respiration and cardiac motion of patient P may continue, unless the patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to point gathering instrument 304 to control insertion motion (e.g., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position Lo on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or another reference value (e.g., 1=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position Li on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position Li of proximal point 316 relative to position Lo. In some examples, position Li may further be used as an indicator of the distance or insertion depth to which distal end 318 of elongate device 310 is inserted into the passageways of the anatomy of patient P.

In an illustrative application, a medical instrument system, such as medical instrument system 200, may include a robotic catheter system for use in lung biopsy procedures. A catheter of the robotic catheter system provides a conduit for tools such as endoscopes, endobronchial ultrasound (EBUS) probes, therapeutic tools, and/or biopsy tools to be delivered to locations within the airways where one or more targets of the lung biopsy, such as lesions, nodules, tumors, and/or the like, are present. When the catheter is driven through anatomy, typically an endoscope is installed such that a clinician, such as operator O, can monitor a live camera view of a distal end of the catheter. The live camera view and/or other real-time navigation information may be displayed to the clinician via a graphical user interface.

Before a biopsy procedure is performed using the robotic catheter system, pre-operative planning steps may be performed to plan the biopsy procedure. Pre-operative planning steps may include segmentation of a patient CT scan to create a three-dimensional (3D) representation (e.g., a 3D model) of anatomy, selecting targets within the 3D model, determining airways in the model, growing the airways to form a connected tree of airways, and planning a path to the targets through the connected tree. One or more of these steps may be performed on the same robotic catheter system used to perform the biopsy, on a different medical instrument system, on a standalone processor, such as a workstation dedicated to pre-operative planning, and/or the like. The plan for the biopsy procedure may be saved (e.g., as one or more digital files) and transferred to the robotic catheter system used to perform the biopsy procedure. The saved plan may include the 3D model, identification of airways, target locations, paths to target locations, points of interest or engagement points, and/or the like. An example of a graphical user interface supporting the pre-operative planning steps is covered in U.S. Patent Application Publication No. 2020/0030044, entitled "Graphical User Interface for Planning a Procedure," and filed on Sep. 20, 2019, which is incorporated by reference in its entirety.

After the plan is transferred to the robotic catheter system, the 3D model of the anatomy may be registered to the actual patient anatomy and/or the catheter within the patient anatomy. Consequently, the real-time position and orientation of the catheter may be projected onto the 3D model and displayed via the graphical user interface. The clinician can then proceed with driving the catheter through anatomy while monitoring navigation progress on the graphical user interface. For example, the clinician may drive the catheter along a predetermined path in the saved plan to navigate to the target location and/or perform a biopsy at a target location.

Illustrative embodiments of a graphical user interface for monitoring a medical procedure, including but not limited to the lung biopsy procedure described above, are provided below. The graphical user interface may include a registration mode that is used to monitor the registration of a 3D model to an anatomy, a navigation mode that is used to monitor the navigation of a medical instrument to a target location in the anatomy, and a performance mode that is used to monitor the performance of an interventional step at the target location. Some aspects of the graphical user interface are similar to features described in International Patent Application Publication No. WO 2018/005861, entitled "Graphical User Interface for Displaying Guidance Information During an Image-Guided Procedure" and filed Jun. 29, 2017; International Patent Application Publication No. WO 2018/005842, entitled "Graphical User Interface for Displaying Guidance Information in a Plurality of Modes During an Image-Guided Procedure" and filed Jun. 29, 2017; and U.S. Patent Application Publication No. US 2020/0054399, entitled "Graphical User Interface for Monitoring an Image-Guided Procedure" and filed on Sep. 30, 2019, which are hereby incorporated by reference in their entirety.

Figure 4:
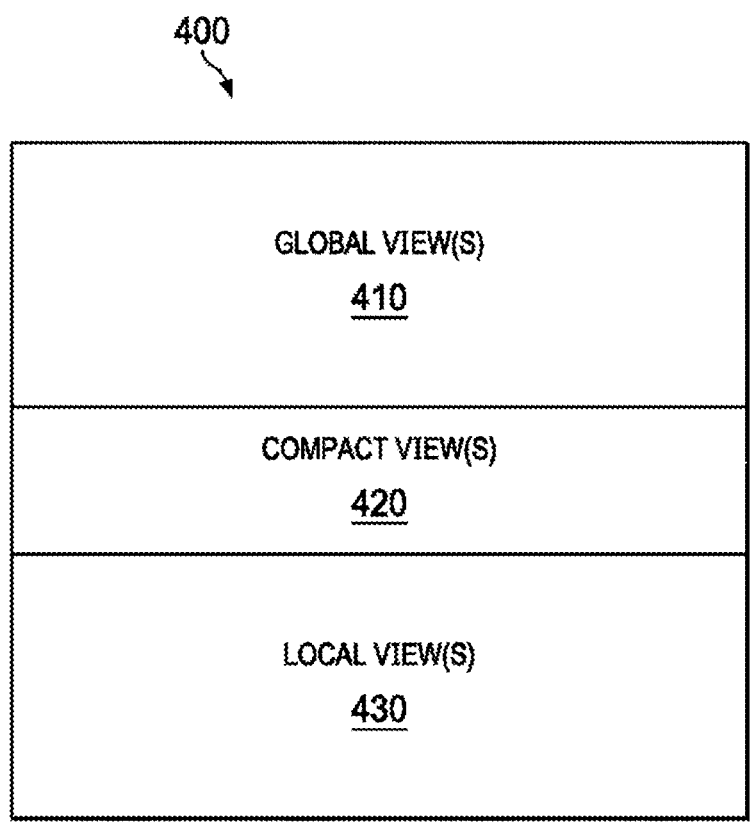
FIG. 4 is a simplified diagram of a graphical user interface displayable on a display system, according to some embodiments.

FIG. 4 is a simplified diagram of a graphical user interface 400 displayable on a display system, such as display system 110, according to some embodiments. Graphical user interface 400 displays information associated with a medical procedure in one or more views that are viewable to a clinician, such as operator O. Although an illustrative arrangement of views is depicted in FIG. 4, it is to be understood that graphical user interface 400 may display any suitable number of views, in any suitable arrangement, and/or on any suitable number of screens. In some examples, the number of concurrently displayed views may be varied by opening and closing views, minimizing and maximizing views, moving views between a foreground and background of graphical user interface 400, switching between screens, and/or otherwise fully or partially obscuring views. Similarly, the arrangement of the views—including their size, shape, orientation, ordering (in a case of overlapping views), and/or the like—may vary and/or may be user-configurable.

In some examples, the views displayed in graphical user interface 400 may be arranged in an organized scheme to facilitate rapid access to relevant information. Although FIG. 4 depicts an illustrative example of one such organization scheme, many other organization schemes are possible. As depicted in FIG. 4, graphical user interface 400 includes an upper portion that displays one or more global views 410, a middle portion that displays one or more compact views 420, and a lower portion that displays one or more local views 430. Global views 410 generally display global aspects of the medical procedure to provide the clinician with a detailed picture of the current state of the medical procedure. Compact views 420 generally display a reduced set of information about the medical procedure in a simplified, uncluttered format to facilitate rapid comprehension by the clinician. Local views 430 generally display local aspects of the medical procedure to monitor movements and/or interventional steps performed by the medical instrument in real-time. Examples of local views 430 are discussed in greater detail below with reference to FIGS. 5A-7.

In some examples, global, compact, and local views 410-430 may be arranged in various configurations other than those depicted in FIG. 4. For example, graphical user interface 400 may have a landscape layout in which global views 410 are positioned on the left, compact views 420 are oriented vertically in the middle, and local views 430 are positioned on the right. In some examples, global, compact, and local views 410-430 may be spread throughout graphical user interface 400, such that graphical user interface 400 may not be divisible into dedicated regions as depicted in FIG. 4. In some examples, graphical user interface 400 may include various views, controls, indicators, and/or the like, in addition to those depicted in FIG. 4. For example, graphical user interface 400 may include a header, footer, one or more sidebars, message bars, popup windows, backgrounds, overlays, and/or the like.

Graphical user interface 400 may be operated in different modes at various stages of the medical procedure. In some examples, the organization scheme may vary based on the mode of graphical user interface 400. In each mode, the arrangement of views may be selected to convey information that is available and/or relevant at the current stage of the medical procedure. In some examples, the modes may include a registration mode, a navigation mode, and/or a performance mode as discussed below. In some examples, various modes may overlap with each other and/or transition seamlessly between each other so as to behave as a single mode. For example, the navigation and performance modes may be seamlessly transitioned such that they may be considered a single hybrid navigation and performance mode.

In some embodiments, graphical user interface 400 can further include one or more interactive user interface elements. For example, in embodiments where display system 110 includes a touch-sensitive display (e.g., a touch screen), graphical user interface 400 could include one or more user interface elements (e.g., buttons, sliders, dials, switches, toggles, and/or the like) that operator O can interact with via touches on the touch-sensitive display, and control system 112 receives the touches as input. That is, the touch-sensitive display is also a control device within medical system 100. The user interface elements could be displayed in one view that is in addition to or in place of any of global, compact, or local views 410-430. Further, in the same embodiments with the touch-sensitive display, operator O could interact with any of global, compact, and/or local views 410-430 as well.

As described above, graphical user interface 400 can operate in a navigation mode that is used to monitor the navigation of a medical instrument to a target location in the anatomy. While in the navigation mode, graphical user interface 400 can include a local view 430 that includes a live camera view of images captured by instrument 104 inside patient P. Local view 430 in navigation mode can also include a virtual view that displays a rendering of the 3D model of the anatomy of patient P (e.g., from the perspective of the distal end of instrument 104) according to a current registration. Local view 430 in navigation mode can further include one or more visual aids to provide navigational information and/or assistance to operator O as operator O navigates instrument 104 within patient P. Examples of local views in navigational mode are described below with reference to FIGS. 5A-7.

In various embodiments, one or more elongate device and/or instrument references can be displayed in a local view 430 (e.g., in a local camera view and/or a virtual view). As used herein, an elongated device and/or instrument reference is a computer-generated graphical or visual representation of the elongate device and/or the instrument at a saved, recorded, created, or planned pose. The elongate device and/or instrument reference can be a 3D representation (e.g., a wireframe model, a rendered 3D object) of the elongate device and/or the instrument. The elongate device reference can be a stylized representation of the elongate device and/or instrument, or a virtual duplicate of the actual elongate device and/or instrument. Further details regarding elongate device and/or instrument references are described below.

Figure 5A:
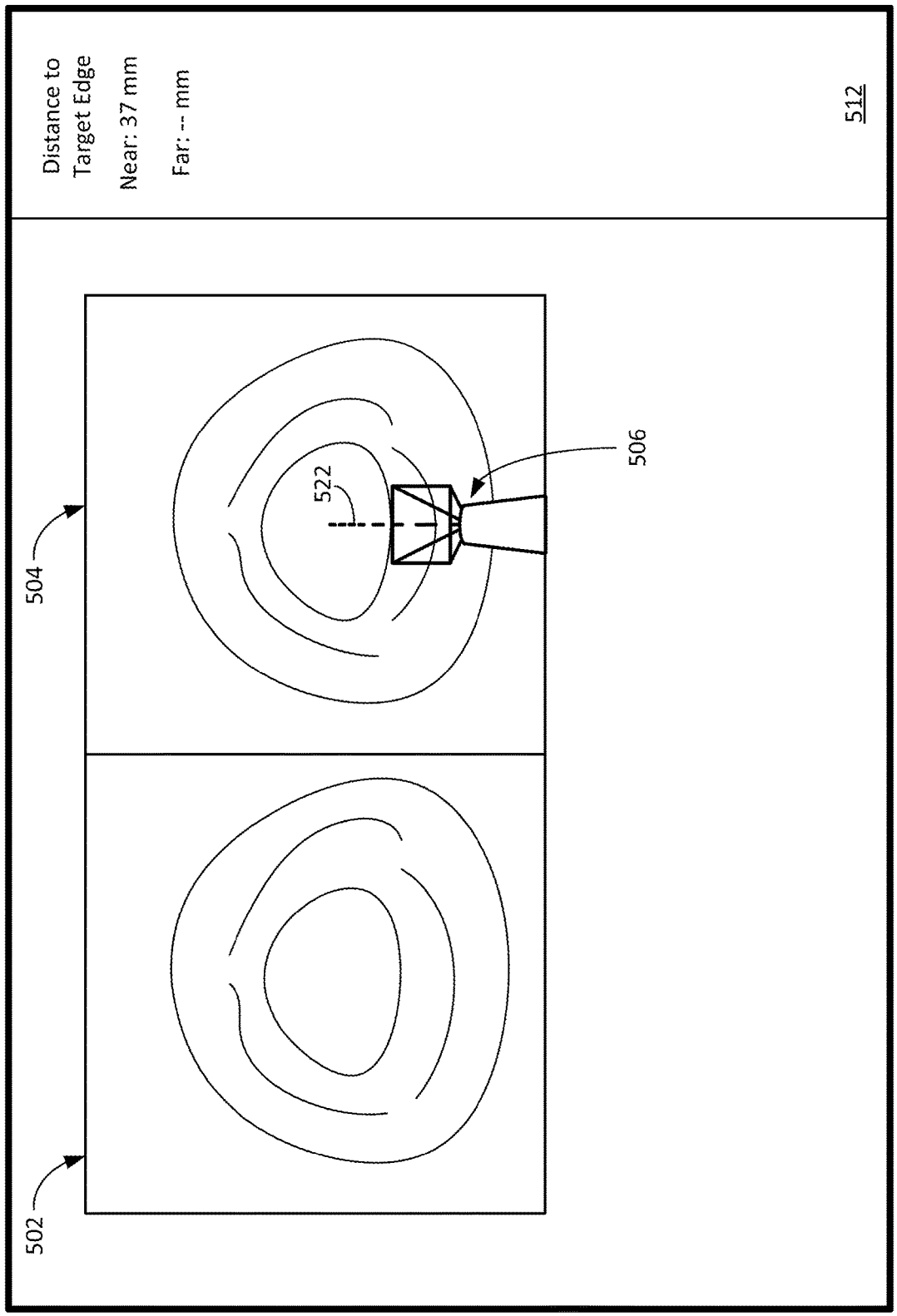
FIGS. 5A-5D are simplified diagrams of an example local view with elongate device references, according to some embodiments.

FIGS. 5A-5D are simplified diagrams of an example local view with elongate device references, according to some embodiments. Local view 500, which is in navigation mode, includes a live camera view 502 and a virtual view 504 displayed side-by-side. Live camera view 502 displays live, real-time images captured at a distal portion (e.g., a distal end) of an elongate device (e.g., instrument 104, elongate device 202, instrument 226, a catheter) within a patient anatomy (e.g., patient P). Live camera view 502 can be captured by an imaging device (e.g., a camera, an endoscope) located at or near the distal portion of the elongate device and/or inserted into the workspace via a lumen (e.g., channel 221) in the elongate device. Live camera view 502 as shown in FIG. 5A is a first-person view from the distal portion of the elongate device. In some embodiments, live camera view 502 can instead show a third-person view, where the camera capturing the live images is slightly behind the distal portion (e.g., the distal end) of the elongate device, and the distal portion of the elongate device is within the field of view of the camera. In some embodiments, the third-person view can be captured by an imaging device that is mounted on an outside of the elongate device or that exits a lumen of the elongate device proximal to the distal portion of the elongate device.

Virtual view 504 is a virtual navigational image that corresponds to a view of the workspace proximate to the elongate device. In some embodiments, virtual view 504 corresponds to the view displayed in live camera view 502 or from the perspective of a related view. Virtual view 504 can be a rendering of a 3D model of the patient anatomy according to a current registration between the 3D model and the patient anatomy. As shown, virtual view 504 corresponds to a third-person view from the perspective of a point slightly behind the distal portion (e.g., the distal end) of the elongate device.

A virtual representation 506 of an elongate device is displayed over virtual view 504. Virtual representation 506 can be a generated virtual 3D object (e.g., wireframe model, rendered 3D object). Virtual representation 506 is associated with the current pose of the elongate device. For example, virtual representation 506 could be displayed at the current pose of the elongate device relative to virtual view 504 of the workspace. In some embodiments, virtual representation 506 includes an orientation pointer 522. Orientation pointer 522 is an extension or projection from the distal end of virtual representation 506 and corresponds to a projection from the distal end of the elongate device. Orientation pointer 522 can provide a visual indication of the orientation of the elongate device (e.g., the direction in which the distal portion of the elongate device is pointing).

Figure 5B:
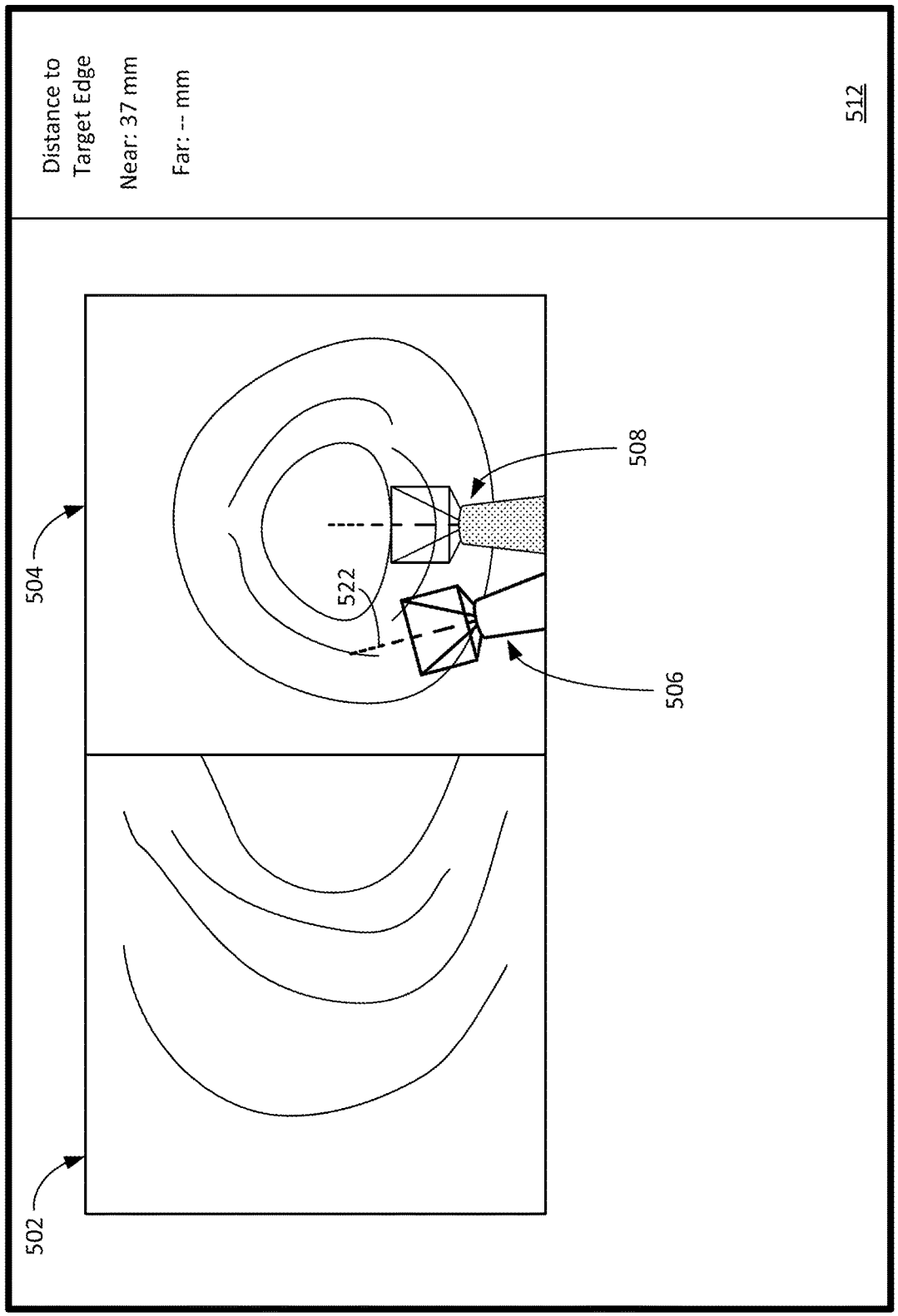

As operator O navigates the elongate device through the patient anatomy, live camera view 502 and/or virtual view 504, including virtual representation 506 associated with the current pose, can be updated accordingly. During the procedure, control system 112 can save or record data from the procedure automatically and/or on command (e.g., on the command of operator O), and the recorded data (e.g., a record or recording of the procedure) can be stored in a storage device. Recorded procedure data from a procedure can be loaded during the same procedure, in a later procedure, and/or outside of a procedure (e.g., during a post-operative review or debrief). Procedure data that can be recorded include, for example, images from live camera view 502 and/or virtual view 504. Procedure data that can be recorded can further include a pose of the elongate device (e.g., the position and/or orientation of the elongate device). More generally, procedure data can include images from a live view from an imaging device associated with the elongate device, images from a virtual view, poses of the elongate device, timestamps associated with the images and/or poses, identifiers of the images and/or poses, an identifier of the operator that operated the elongate device, and/or the like. For example, the current pose of the elongate device in FIG. 5A can be saved on the command of operator O to control system 112. After control system 112 has saved the current pose in FIG. 5A, operator O can move the elongate device to a different pose, for example as shown in FIG. 5B. In FIG. 5B, virtual representation 506 of the elongate device is displayed at the (new) current pose of the elongate device relative to virtual view 504, which is different than the pose of the elongate device as shown in FIG. 5A. Further, an elongate device reference 508 of the elongate device can be displayed over virtual view 504 concurrently with virtual representation 506. Elongate device reference 508 is associated with the saved pose from FIG. 5A and is displayed at that saved pose relative to virtual view 504. Elongate device reference 508 can be visually distinct from virtual representation 506 by color, shading, labeling, and/or the like. Elongate device reference 508 can also include an orientation pointer 522.

Figure 5C:
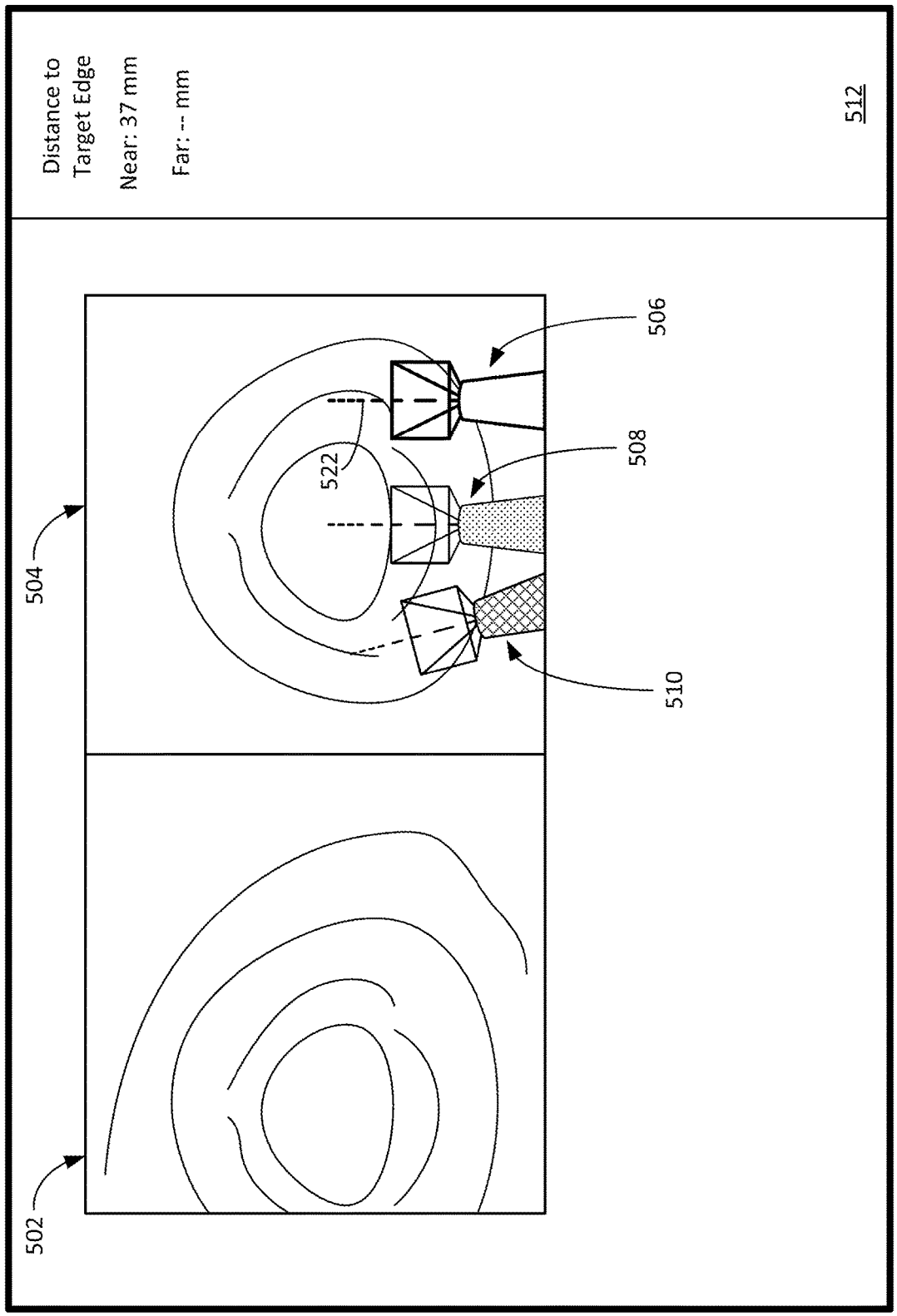

The operator can command control system 112 to save multiple different poses of the elongate device. Control system 112 can display elongate device references associated with one or more different saved poses along with the virtual representation corresponding to the current pose concurrently. Accordingly, for example, control system 112 could save the current pose of the elongate device as shown in FIG. 5B, and afterwards operator O can move the elongate device to another pose. As shown in FIG. 5C, elongate device reference 510 is displayed over virtual view 504. Elongate device reference 510 is associated with the saved pose from FIG. 5B and is displayed at that saved pose relative to virtual view 504. Also as shown in FIG. 5C, virtual representation 506 is displayed at the (new) current pose relative to virtual view 504, and elongate device reference 508 continues to be displayed at its corresponding saved pose relative to virtual view 504. Elongate device reference 510 can also include an orientation pointer 522. Virtual representation 506 and elongate device references 508 and 510 can be visually distinct from each other by, for example, color, shading, labeling, and/or the like. In some embodiments, an elongate device reference associated with a saved pose can be omitted from being displayed. Omitted elongate device references can include elongate device references associated with a saved pose that is behind the current pose or whose distance from the current pose is beyond a threshold. Further, the display size of an elongate device reference associated with a saved pose can be determined based on the distance of the corresponding saved pose from the current pose. Accordingly, the sizes of elongate device references can be scaled to provide perspective-like effects that can indicate distance from the current pose.

Figure 5D:
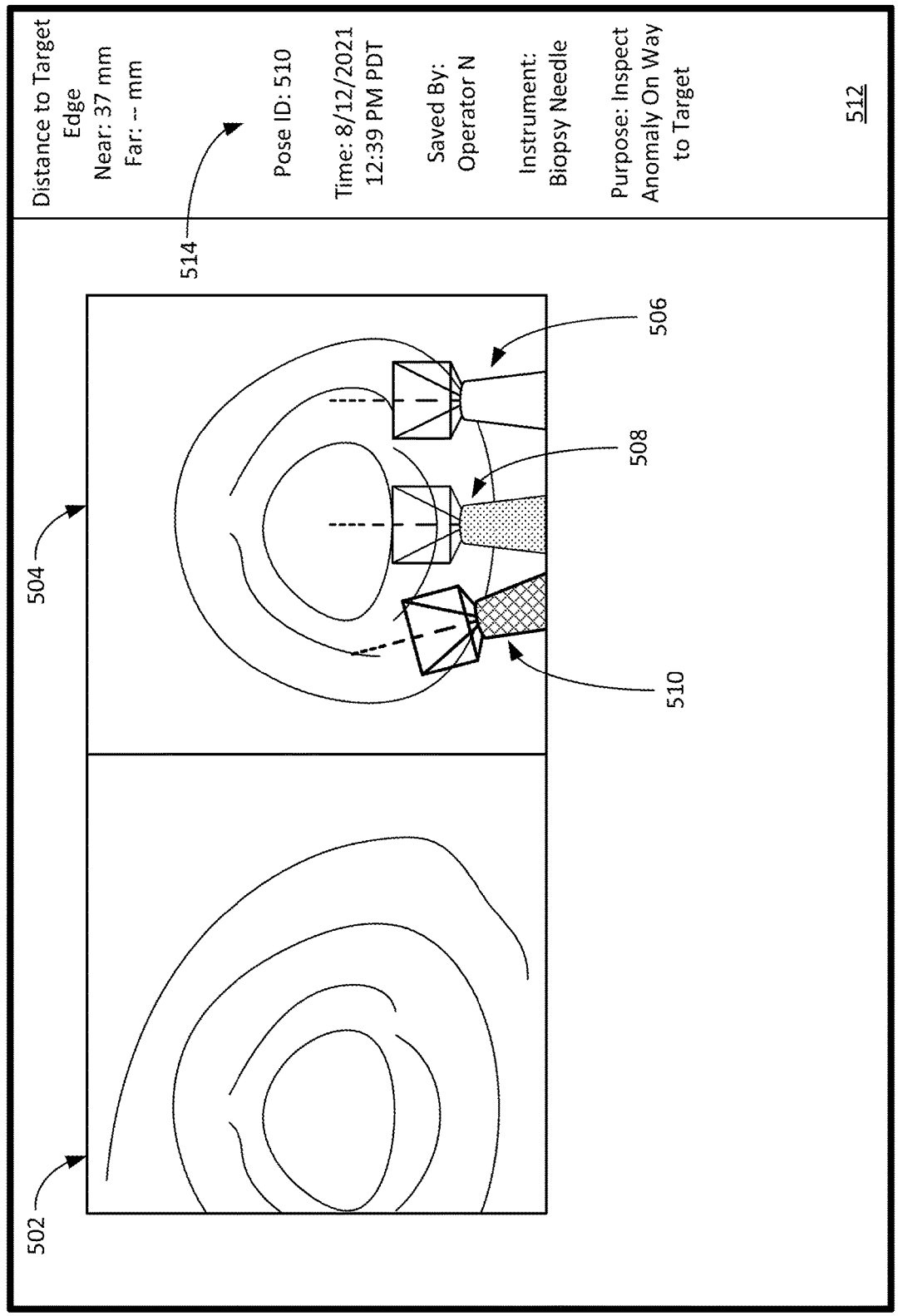

In some embodiments, an elongate device reference associated with a saved pose can include associated metadata. The metadata can include, for example, an identifier (e.g., a unique identifier) of the saved pose, a timestamp of the saved pose (e.g., timestamp of when the pose was saved), the operator or other user who saved or created the saved pose, information regarding a specific instrument within and/or extending from the elongate device when the pose was saved, a description of the saved pose (e.g., information or notes regarding a purpose for which the pose was saved), and/or other information associated with the saved pose. During the procedure, operator O can select an elongate device reference (e.g., by clicking or tapping on the elongate device reference, selecting the reference from a menu, cycling through the displayed references) to view the metadata associated with the corresponding saved pose of the elongate device reference. A selected elongate device reference can be visually changed to indicate the selection (e.g., highlighted, flashed, changed in color, etc.). For example, as shown in FIG. 5D, operator O has selected elongate device reference 510. Metadata 514 associated with the corresponding saved pose of elongate device reference 510 can be displayed in an information sidebar 512 in local view 500. Metadata 514, as shown, includes an identifier of the saved pose (e.g., "Pose ID"), a timestamp of the corresponding saved pose, identification of the operator or user who saved or created the saved pose (e.g., "Saved By"), a specific instrument associated or utilized with the elongate device when the pose was saved (e.g., "Instrument"), which can be the same or different instrument than an instrument associated with the current pose of the elongate device, and/or a note regarding the purpose of the saved pose (e.g., "Purpose"). In some embodiments, metadata associated with an elongate device reference can include more or fewer fields than those described above with respect to metadata 514. Other possible metadata can include the model of the elongate device, the model of the instrument, etc. In some embodiments, at least a portion of the metadata can be input by an operator. For example, the operator saving a pose associated with the elongate device reference during a procedure can input metadata indicating a purpose of the pose (e.g., why the elongate device was at that pose, observations associated with the pose that may warrant further attention or follow up).

In some embodiments, additional data associated with the selected elongate device reference can be displayed in information sidebar 512. Control system 112 can determine the positional and/or orientational differences in one or more degrees of freedom between the pose associated with a selected elongate device reference (e.g., the pose associated with elongate device reference 510 in FIG. 5D) and the current pose of the elongate device (e.g., the pose associated with virtual representation 506) and display information indicating those differences in information sidebar 512. The information can include distance values and headings or directions, in one or more degrees of freedom of the pose associated with the selected elongate device reference relative to the current pose of the elongate device. The distance values and headings/directions can be expressed in any suitable unit and/or coordinate or reference frame. For example, distance values could be expressed in millimeters. As another example, headings could be expressed as positive or negative directions along axes (x, y, z) in a Cartesian coordinate frame, as cardinal directions (e.g., north, south, east, west, up, down), as anatomical directions (e.g., anterior, posterior, superior, inferior, medial, lateral), and/or as directions along degrees of freedom (e.g., left/right, up/down, in/out, roll, pitch, yaw). The positional and/or orientational difference information can provide operator O further navigational assistance by quantifying the difference between the current pose and a saved or planned pose. For example, the positional and/or orientational difference information can assist operator O in articulating the elongate device so that the pose of the elongate device aligns with the pose of the selected elongate device reference.

Referring back to FIG. 5A, in some embodiments, orientation pointer 522 can provide a visual indication of the orientation of the elongate device. For example, orientation pointer 522 could represent a projection from the distal end of the elongate device. In some embodiments, orientation pointer 522 can provide a visual indication of the orientation, and also the extent and range (e.g., the reach when extended from the elongate device, up to and including full extension), of an instrument (e.g., instrument 226) that is extended from the elongate device. The orientation of the instrument can be different from the orientation of the elongate device. Further details about orientation pointers are described below with reference to FIGS. 8A-8B.

It should be appreciated that poses can be saved during a procedure and/or planned prior to a procedure. For example, during pre-operative planning, planned poses of the elongate device and/or instrument (e.g., specific poses for performing a task during the procedure) can be created and/or generated and saved in a plan that is created in the pre-operative planning. The planned poses can be loaded from the plan before or during a procedure, and elongate device references corresponding to the planned poses can be displayed during the procedure similarly to elongate device references corresponding to saved poses. Saved poses and planned/created poses may be more generally referred to below as a "reference pose" or "reference poses."

In some embodiments, one or more points of interest (e.g., engagement points, biopsy points, etc.) in the workspace (e.g., patient anatomy) can be saved during a procedure (e.g., prior or current procedure) and/or created during pre-operative planning and loaded from a plan that is created in the pre-operative planning. A point of interest can be a target point for a task or engaging an instrument during the procedure (e.g., a biopsy point, an engagement point) and/or an observational point for potential further follow-up (e.g., an unexpected anomaly on the way to another target). Further, a point of interest can be associated with metadata and be optionally associated with an elongate device reference corresponding to a reference pose.

Figure 6:
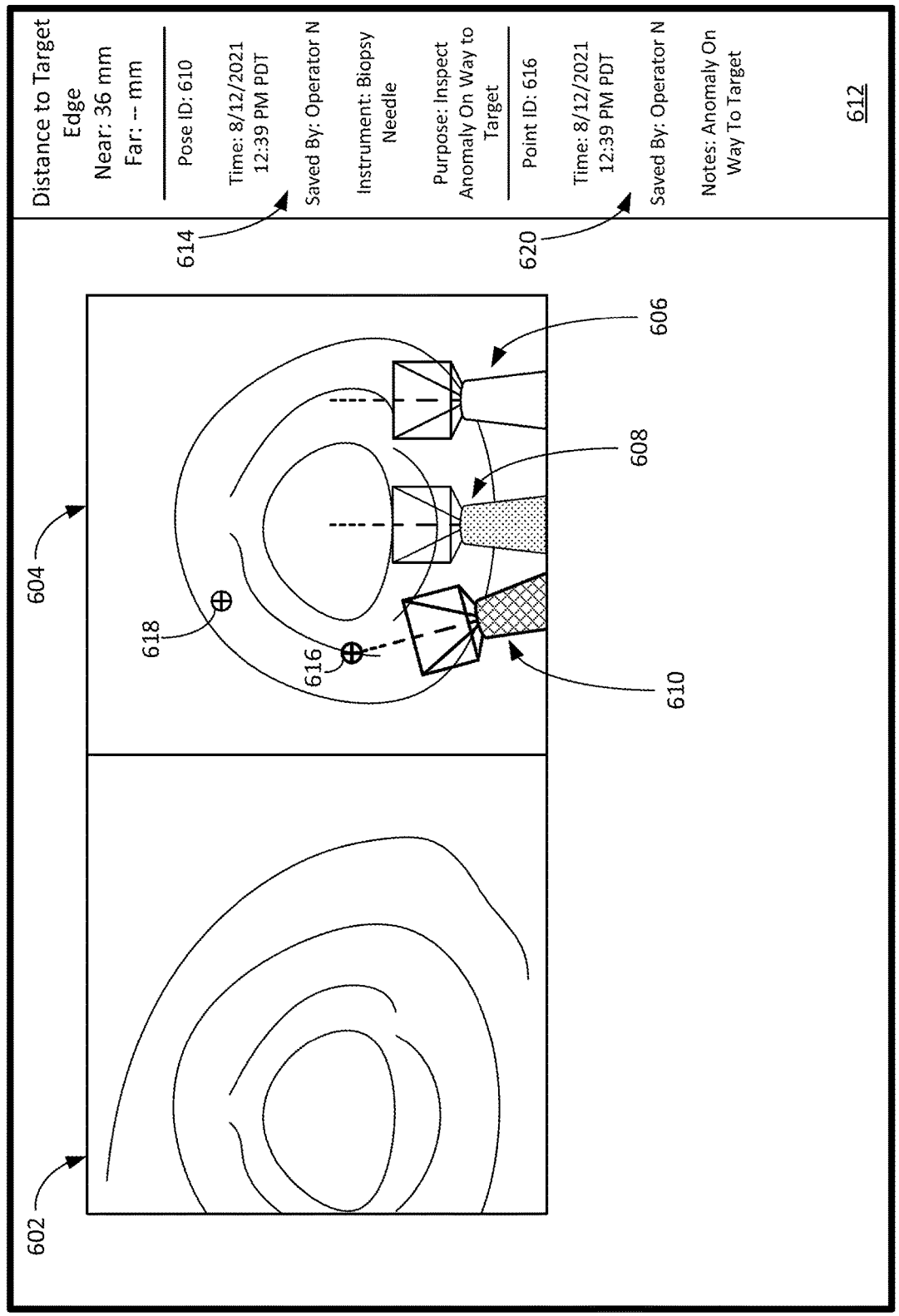
FIG. 6 is a simplified diagram of example local view with elongate device references and an associated point of interest, according to some embodiments.

FIG. 6 is a simplified diagram of example local view with an elongate device reference and an associated point of interest, according to some embodiments. As shown, local view 600 includes a live camera view 602, a virtual view 604, and an information sidebar 612. Virtual representation 606 of an elongate device, corresponding to the current pose of the elongate device, as well as elongate device references 608 and 610 corresponding to respective reference poses of the elongate device, are displayed on virtual view 604. As shown, elongate device reference 610 is selected, and associated metadata 614 is displayed in information sidebar 612.

Also displayed in virtual view 604 are points of interest 616 and 618. Points of interest (e.g., points of interest 616 and 618) can be loaded from a saved plan and/or recorded data of a prior procedure or the current procedure. Point of interest 616 is associated with elongate device reference 610, and elongate device reference 610 is pointed toward point of interest 616. For example, point of interest 616 could be a target point for engagement by an instrument associated with elongate device reference 610 or an observation point observed at the reference pose associated with elongate device reference 610. With the selection of elongate device reference 610, associated point of interest 616 is selected as well, and metadata 620 associated with point of interest 616 can be displayed in information sidebar 612 along with metadata 614 associated with elongate device reference 610. Metadata 620 associated with point of interest 616 can include, for example, an identifier of the point of interest (e.g., "Point ID"), a timestamp, identification of the operator or user who saved or created the point of interest (e.g., "Saved By"), and/or a description of or notes regarding the point of interest (e.g., purpose of the point of interest, observations about the point, etc.). In some embodiments, metadata associated with a point of interest can include more or fewer fields than those described above with respect to metadata 620.

Point of interest 618, as shown, is not associated with any particular elongate device reference. Operator O can navigate the elongate device toward the point in the patient anatomy corresponding to point of interest 618, using point of interest 618 and virtual representation 606 in virtual view 604 as navigational assistance.

While the above description describes elongate device references and points of interest being displayed over a virtual view, it should be appreciated that elongate device references and points of interest can be displayed over a live camera view in addition or alternatively to displaying them over a virtual view. An example of an elongate device reference that is displayed over a live camera view is described below.

Figure 7:
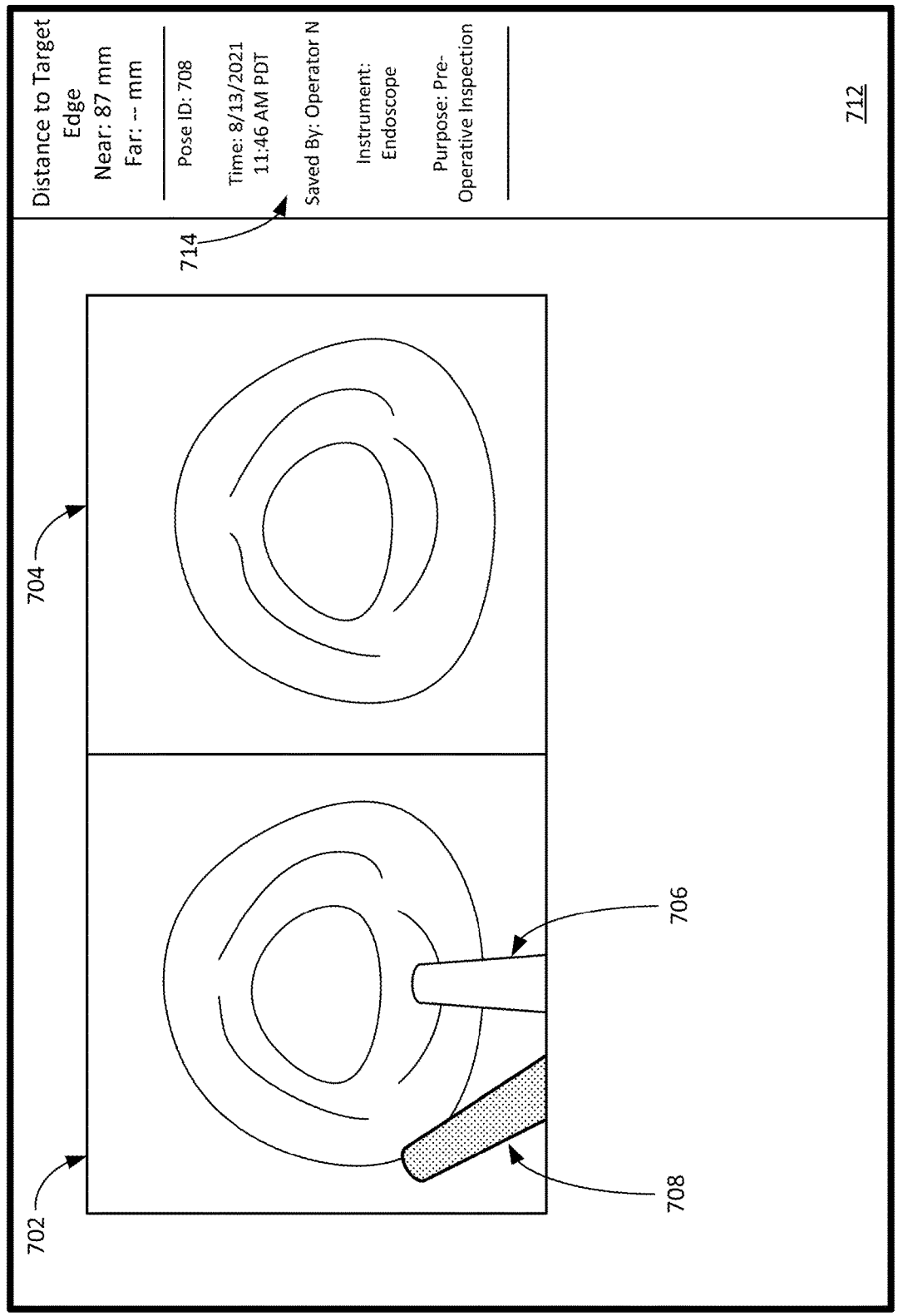
FIG. 7 is a simplified diagram of an example local view with an elongate device reference displayed over a live camera view, according to some embodiments.

FIG. 7 is a simplified diagram of an example local view with an elongate device reference displayed over a live camera view, according to some embodiments. As shown, local view 700 includes a live camera view 702, a virtual view 704, and an information sidebar 712. Live camera view 702 is shown in a third-person view, in which the distal portion of elongate device 706 is captured and visible in the live images of live camera view 702. The imaging device capturing images for live camera view 702 can be mounted on an outside of the elongate device or can exit a lumen of the elongate device proximal to the distal portion of the elongate device. An elongate device reference 708 is displayed over live camera view 702. Elongate device reference 708 is associated with a reference pose of elongate device 706. As shown, elongate device reference 708 is a representation whose shape resembles elongate device 706 (e.g., elongate device reference 708 is a virtual duplicate of elongate device 706). Alternatively, in some embodiments, elongate device reference 708 can be a stylized representation of elongate device 706. Although not shown, an orientation pointer providing a visual indication of a pointing direction and/or a reach of an instrument extending (or extendable) from elongate device reference 708 can also be shown on the live camera view 702, similar to the orientation pointers described above (e.g., orientation pointer 522).

As shown in FIG. 7, elongate device reference 708 has been selected by operator O, and metadata 714 associated with elongate device reference 708 is displayed in information sidebar 712. Operator O can navigate elongate device 706 to the reference pose associated with elongate device reference 708 by navigating elongate device 706 as shown in live camera view 702 to align with elongate device reference 708.

While the above-described embodiments describe displaying elongate device references in third-person views, it should be appreciated that elongate device references can be displayed in first-person views as well. In a first-person view, a virtual representation corresponding to the current pose of the elongate device can be omitted or projected distally from the distal portion of the elongate device, and one or more elongate device references corresponding to reference poses can be displayed on a live camera view or a virtual view. Operator O can navigate the elongate device to a reference pose associated with an elongate device reference in the first person view by navigating the elongate device such that the live camera view and/or the virtual view aligns with the elongate device reference. In some examples, an elongate device reference displayed in a first-person view can include, with or without a virtual representation of the elongate device itself, an orientation pointer providing a visual indication of a pointing direction and/or a reach of an instrument extending (or extendable) from the elongate device.

Figure 8A:
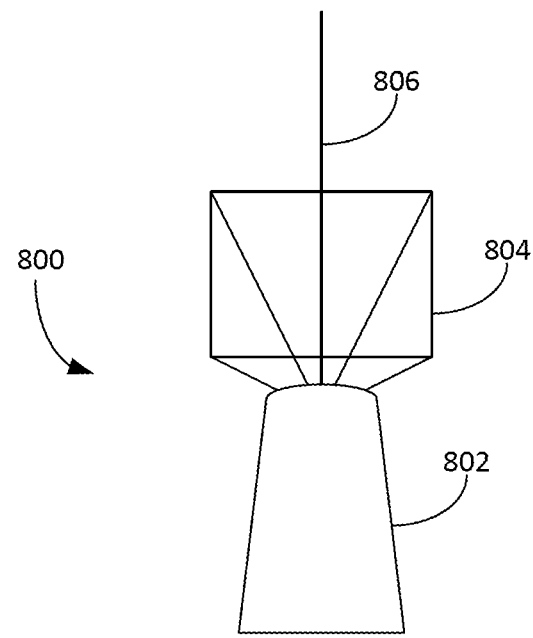
FIGS. 8A-8B illustrate examples of elongate device references, according to some embodiments.
Figure 8B:
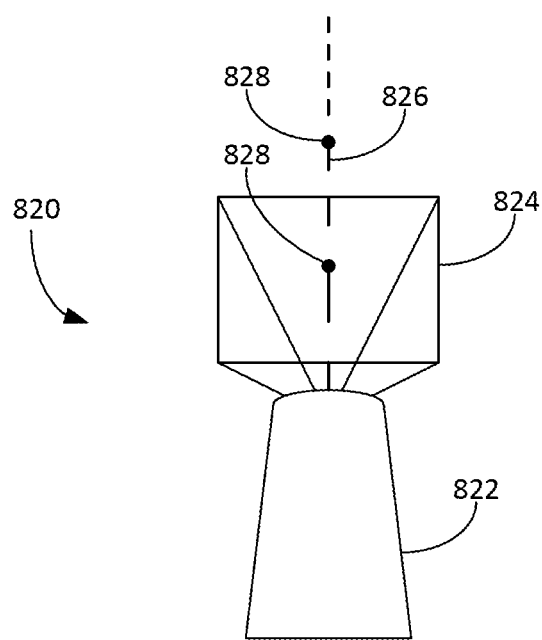

FIGS. 8A-8B illustrate examples of elongate device references, according to some embodiments. Elongate device references 800 and 820 are examples of stylized elongate device references. Other elongate device references can be virtual duplicates of the elongate device and/or instrument in use during the procedure or when the corresponding reference pose was saved or planned. Elongate device reference 800 or 820 can be 3D objects generated by control system 112.

As shown, elongate device reference 800 includes a body 802 that represents a distal portion of the elongate device. A shape 804 representing a field of view from the distal end of the elongate device projects outward from body 802. As shown, shape 804 has a pyramid-like shape. In some embodiments, shape 804 can be any suitable shape (e.g., a cone shape, a pyramid-like shape with a triangular base). An orientation pointer 806 indicating the orientation of the distal portion (e.g., the distal end) of the elongate device also projects outward from body 802.

As shown, elongate device reference 820 includes a body 822 that represents a distal portion of the elongate device, similar to body 802. A shape 824 representing a field of view from the distal end of the elongate device projects outward from body 822, similar to shape 804. In some embodiments, shape 804/824 can be omitted from elongate device reference 800/820.

An orientation pointer 826 indicating the orientation of the distal portion of the elongate device also projects outward from body 822. In some embodiments, orientation pointer 806 or 826 can also represent an instrument extending from the distal portion of the elongate device (e.g., instrument 226) and can have a visual appearance resembling the instrument. For example, if the instrument is a straight needle-like instrument, then the orientation pointer could be represented as a straight line, as with orientation pointer 806 or 826. As another example, if the instrument is a clamping instrument, the orientation pointer can resemble the clamping instrument. Orientation pointer 806/826, when representing an instrument, can be associated with a current or reference pose of the instrument and be displayed in the elongate device reference according to that instrument pose. In some other embodiments, the orientation pointer can be omitted.

The orientation pointer can be represented with solid line(s) (e.g., orientation pointer 806) or with dotted or broken line(s) (e.g., orientation pointer 826). In some embodiments, the orientation pointer can include distance/length references or markers. The distance/length references or markers can indicate the distance/length from the distal end of the elongate device and/or a distance/length on the instrument extendable or extending from the elongate device. For example, dots 828 on orientation pointer 826 could mark 10-mm increments. Other examples of distance/length references or markers include hash marks similar to those on a ruler. The distance/length markers can include markers of larger unit increments and markers of smaller unit increments (e.g., small dots for 1-mm increments and large dots for 10-mm increments).

In some embodiments, elongate device references, and the virtual representation of the elongate device corresponding to the current pose, can be color-coded, numbered, labeled, or otherwise identified and/or differentiated from each other. Accordingly, when those elongate device references and/or the virtual representation are displayed, operator O can distinguish them more easily. For example, each elongate device reference that is concurrently displayed can have a body 802/822 with a different color, and the virtual representation can have a distinct color as well.

Figure 9:
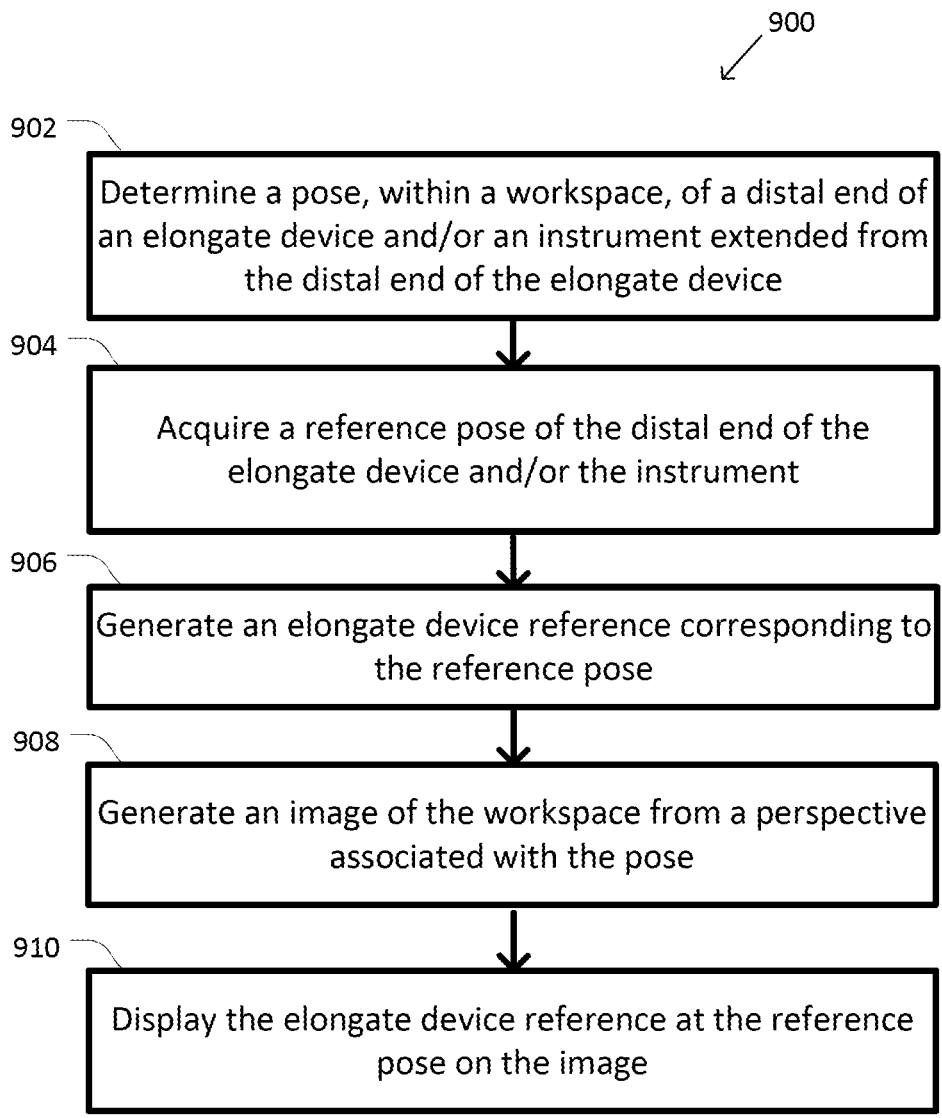
FIG. 9 is a flow chart of method steps for providing an elongate device reference, according to some embodiments.

FIG. 9 is a flow chart of method steps for providing an elongate device reference, according to some embodiments. Although the method steps are described with respect to the systems of FIGS. 1-8B, persons skilled in the art will understand that any system configured to perform the method steps, in any order, falls within the scope of the various embodiments. In some embodiments, one or more of the steps 902-910 of method 900 may be implemented, at least in part, in the form of executable code stored on one or more non-transient, tangible, machine readable media that when run by one or more processors (e.g., one or more processors of control system 112) would cause the one or more processors to perform one or more of the steps 902-910.

As shown, method 900 begins at step 902, where control system 112 determines a pose, within a workspace, of a distal portion of an elongate device and/or an instrument extended from the distal portion of the elongate device. In some embodiments, the elongate device can correspond to instrument 104, elongate device 202, a catheter, and/or the like. The instrument extended from the distal portion of the elongate device can correspond to instrument 226. Control system 112 can determine a current pose (e.g., current position and/or orientation) of an elongate device and/or the instrument within the workspace (e.g., within a passageway in the patient anatomy of patient P). Control system 112 can determine the pose of the elongate device and/or the instrument by, for example, obtaining data from sensor system 108.

At step 904, control system 112 can acquire a reference pose of the distal portion of the elongate device and/or the instrument. Control system 112 can load a reference pose of the elongate device and/or the instrument from a preoperative plan or a pose previously recorded during the current or a prior procedure. In some instances, the reference pose may be the pose of the elongate device and/or instrument determined in step 902. The reference pose may be acquired in response to a command of operator O to, for example, save the reference pose.

At step 906, control system 112 can generate an elongate device reference corresponding to the reference pose. Control system 112 can generate a 3D object (e.g., elongate device reference 508 or 510) that is a stylized representation (e.g., elongate device reference 800 or 820) or a virtual duplicate (e.g., elongate device reference 708) of the elongate device. The 3D object can be displayed at a position and orientation corresponding to the reference pose on a live camera view and/or a virtual view.

At step 908, control system 112 can generate an image of the workspace from a perspective associated with the pose determined in step 902. Control system 112 can generate a virtual view (e.g., virtual view 504, 604, or 704) based on the current pose of the elongate device and a 3D model of the workspace (e.g., a patient anatomy) according to a current registration. Additionally or alternatively, control system 112 can capture images from an imaging device associated with the elongate device for a live camera view (e.g., live camera view 502, 602, or At step 910, control system 112 can display the elongate device reference at the reference pose on the image. Control system 112 displays an elongate device reference associated with the reference pose (e.g., any of elongate device references 508, 510, 608, 610, or 708) at the reference pose on the virtual view (e.g., virtual view 504, 604, or 704) and/or the live camera view (e.g., live camera view 502, 602, or 702). In some embodiments, control system 112 can also concurrently display metadata associated with an elongate device reference (e.g., metadata 514 and 614 associated with a selected elongate device reference 510 and 610 respectively). In some embodiments, control system 112 can also concurrently display a point of interest (e.g., point of interest 616 associated with selected elongate device reference 610, point of interest 618) and optionally metadata associated with a point of interest (e.g., metadata 620). In some embodiments, control system 112 can concurrently display the elongate device reference with a virtual representation associated with the current pose of the elongate device. For example and with reference to FIG. 5B, the control system 112 could concurrently display elongate device reference 508 with a virtual representation 506 associated with the current pose of the elongate device.

In some embodiments, one or more of the steps of method 900 can be repeated as needed to display an elongate device reference at another reference pose. In some embodiments, multiple elongate device references corresponding to different reference poses can be displayed concurrently along with a representation (virtual representation or image capture) of the elongate device corresponding to the current pose.

Figure 10:
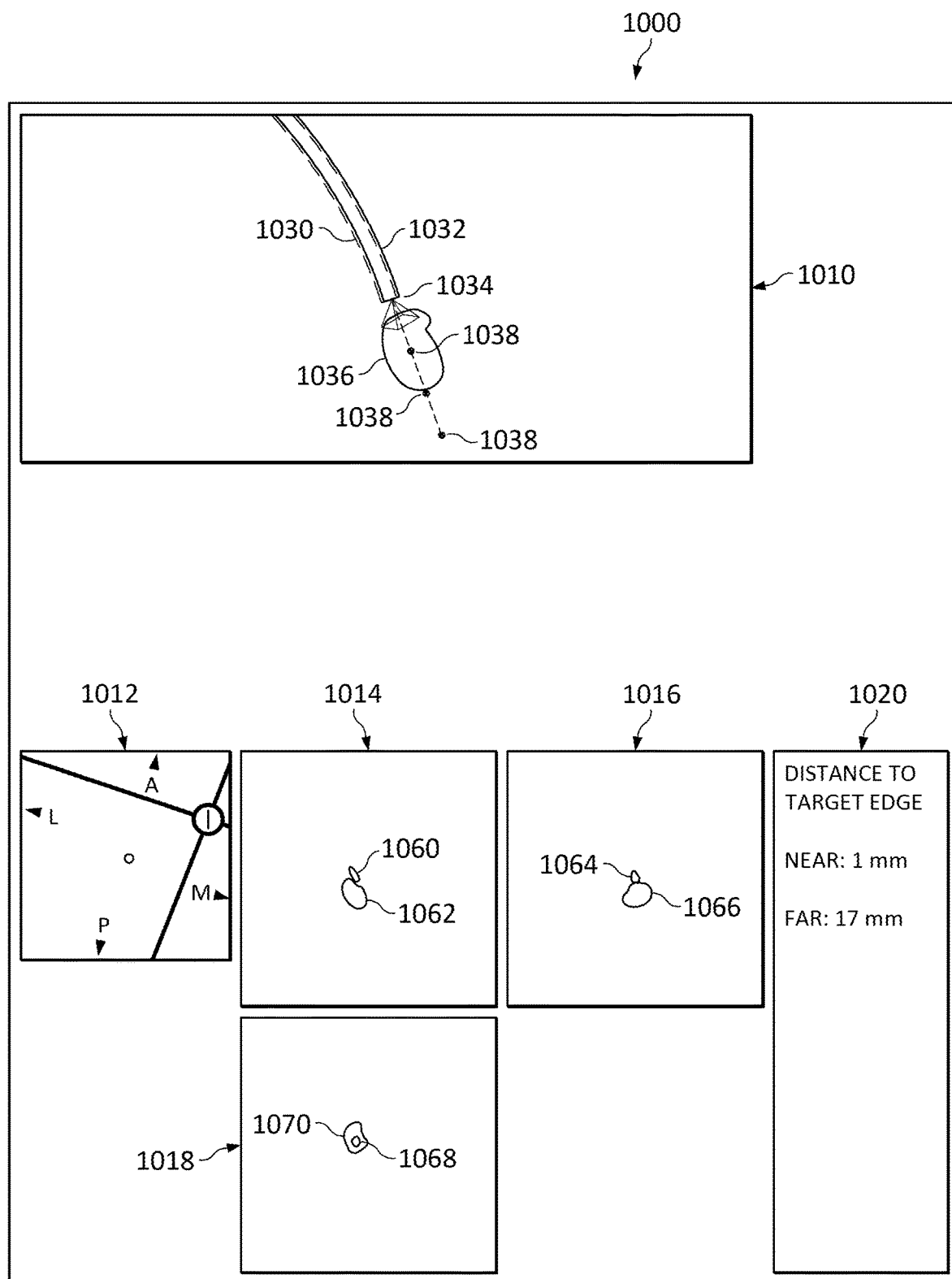
FIG. 10 illustrates a simplified diagram of a graphical user interface that includes a coronal view of an elongate device, according to some embodiments.

FIG. 10 illustrates a simplified diagram of a graphical user interface that includes a coronal view of an elongate device, according to some embodiments. The graphical user interface 1000 includes, without limitation, a global view 1010 and a local view that further includes a virtual view 1012, a coronal view 1014, a sagittal view 1016, an axial view 1018, and an information sidebar 1020.

Global view 1010 displays a reference view 1030 with coronal perspective of the elongate device that represents a pose of the elongate device at a fixed point of time. Global view 1010 further displays a live current view 1032 with coronal perspective of the elongate device as the operator O articulates the elongate device. Global view 1010 displays a representation of a distal end 1034 of the elongate device. Global view 1010 further displays the target location 1036 as determined from one or more anatomical models of the patient anatomy. As shown, the live current view 1032 of the elongate device along with the target location 1036 from the one or more anatomical models assists operator O in navigating the elongate device toward the target location 1036. Distance indicators 1038 show distance markers at distance increments of 1 cm, 2 cm, and 3 cm from the distal end 1034 of the elongate device.

Virtual view 1012 provides an orientation guide indicating the pose of the elongate device. Virtual view 1012 includes equator lines that intersect at a location shown as 'I.' The equator lines can include heading indicators indicating the anatomical directions/headings. A first equator line includes an anterior heading indicator 'A' and a posterior heading indicator 'P.' A second equator line includes a medial heading indicator 'M' and a lateral heading indicator 'L.' The heading indicators provide navigational information and guidance to operator O as operator O monitors the patient anatomy and navigates the elongate device through the patient anatomy.

Coronal view 1014, sagittal view 1016, and axial view 1018 are images acquired from an intraoperative image data set of anatomic passageways, such as a CBCT scan. Coronal view 1014 is a coronal view image acquired from the image data set. Coronal view 1014 includes a coronal image 1060 of the distal end of the elongate and a coronal image 1062 of the target location. As can be seen by comparing global view 1010 and coronal view 1014, the target location 1036 from the one or more anatomical models relative to the distal end 1034 of the elongate device in global view 1010 is not consistent with the location of the coronal image 1062 of the target location relative to coronal image 1060 of the distal end of the elongate device. This can occur, for example, due to movement and/or changes in the patient anatomy between the creation of the one or more anatomical models and the live procedure. Sagittal view 1016 is a sagittal view image acquired from the image data set. Sagittal view 1016 includes a sagittal image 1064 of the distal end of the elongate and a sagittal image 1066 of the target location. Axial view 1018 is an axial view image acquired from the image data set. Axial view 1018 includes an axial image 1068 of the distal end of the elongate and an axial image 1070 of the target location.

As described herein, control system 112 can determine the positional and/or orientational differences in one or more degrees of freedom between the reference view 1030 of the elongate device and the current view 1032 of the elongate device and display information indicating those differences in information sidebar 1020. The information can include distance values and headings or directions, in one or more degrees of freedom of the reference view 1030 of the elongate device relative to the current view 1032 of the elongate device.

Figure 11:
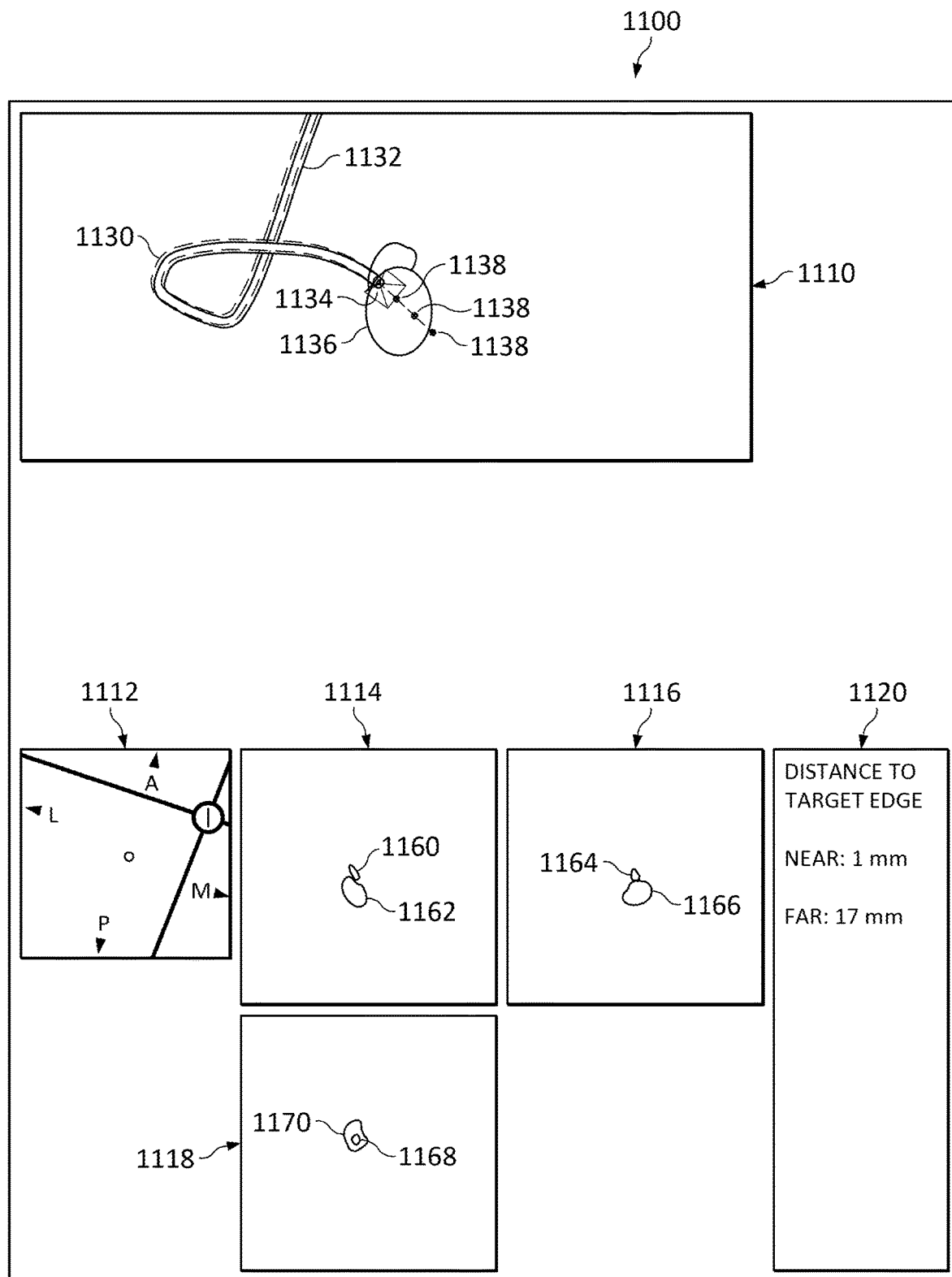
FIG. 11 illustrates a simplified diagram of a graphical user interface that includes an axial view of an elongate device, according to some embodiments.

To aid in articulating the elongate device, the operator O can switch global view 1010 to show a different view of the elongate device. In that regard, FIG. 11 illustrates a simplified diagram of a graphical user interface that includes an axial view of an elongate device, according to some embodiments. The graphical user interface 1100 includes, without limitation, a global view 1110 and a local view that further includes a virtual view 1112, a coronal view 1114, a sagittal view 1116, an axial view 1118, and an information sidebar 1120.

Global view 1110 displays a reference view 1130 with axial perspective of the elongate device that represents a pose of the elongate device at a fixed point of time. Global view 1110 further displays a live current view 1132 with axial perspective of the elongate device as the operator O articulates the elongate device. Global view 1110 displays a representation of a distal end 1134 of the elongate device. Global view 1110 further displays the target location 1136 as determined from one or more anatomical models of the patient anatomy. As shown, the live current view 1132 of the elongate device along with the target location 1136 from the one or more anatomical models assists operator O in navigating the elongate device toward the target location 1136. Distance indicators 1138 show distance markers at distance increments of 1 cm, 2 cm, and 3 cm from the distal end 1134 of the elongate device.

Virtual view 1112 provides an orientation guide indicating the pose of the elongate device, as described herein. Coronal view 1114 acquired from the image data set includes a coronal image 1160 of the distal end of the elongate and a coronal image 1162 of the target location. Sagittal view 1116 acquired from the image data set includes a sagittal image 1164 of the distal end of the elongate and a sagittal image 1166 of the target location. Axial view 1118 acquired from the image data set includes an axial image 1168 of the distal end of the elongate and an axial image 1170 of the target location. Control system 112 can determine the positional and/or orientational differences in one or more degrees of freedom between the reference view 1130 of the elongate device and the current view 1132 of the elongate device and display information indicating those differences in information sidebar 1120.

Figure 12:
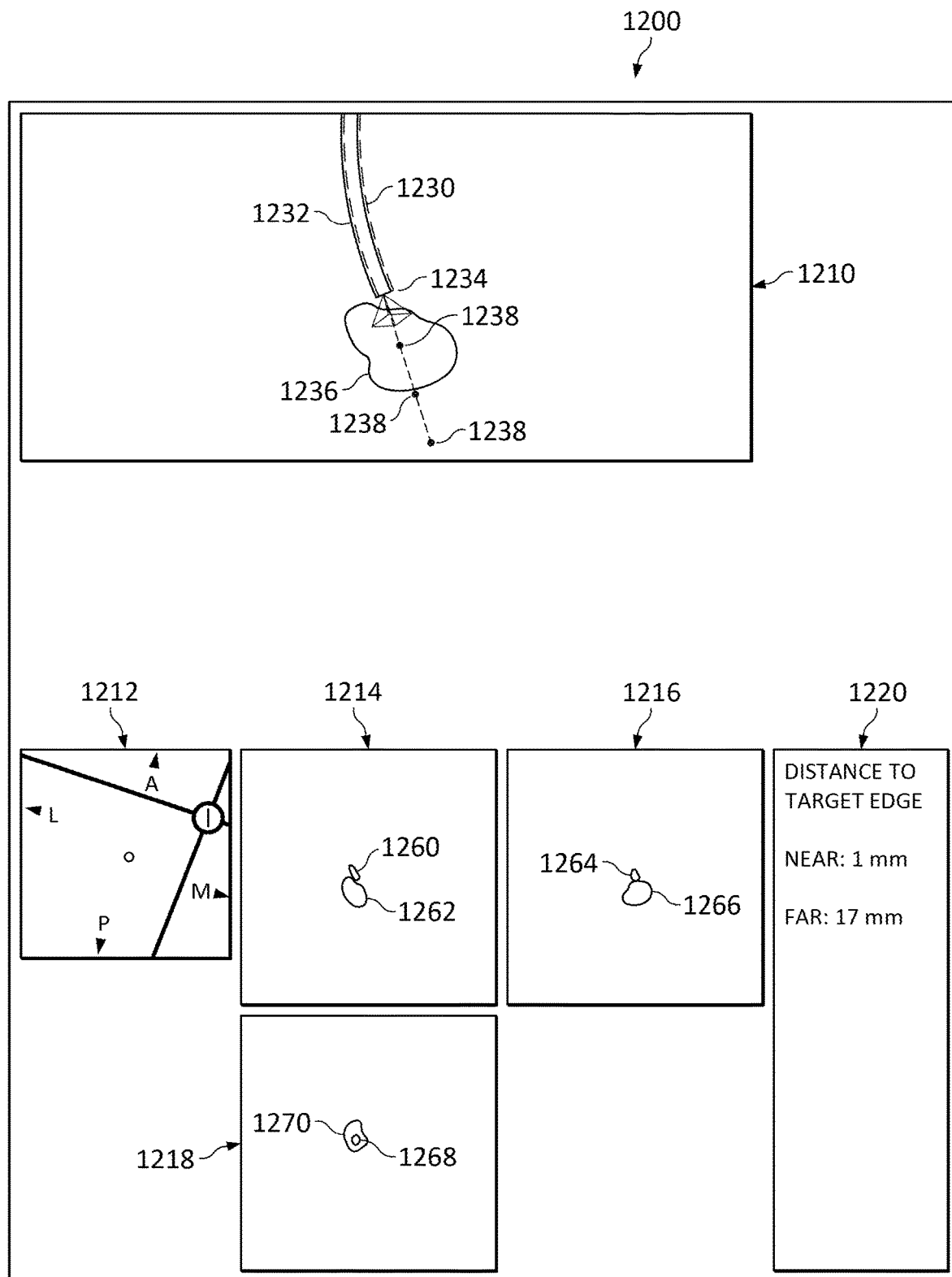
FIG. 12 illustrates a simplified diagram of a graphical user interface that includes a sagittal view of an elongate device, according to some embodiments.

The operator O can further switch global view 1110 to yet another different view of the elongate device. In that regard, FIG. 12 illustrates a simplified diagram of a graphical user interface that includes a sagittal view of an elongate device, according to some embodiments. The graphical user interface 1200 includes, without limitation, a global view 1210 and a local view that further includes a virtual view 1212, a coronal view 1214, a sagittal view 1216, an axial view 1218, and an information sidebar 1220.

Global view 1210 displays a reference view 1230 with sagittal perspective of the elongate device that represents a pose of the elongate device at a fixed point of time. Global view 1210 further displays a live current view 1232 with sagittal perspective of the elongate device as the operator O articulates the elongate device. Global view 1210 displays a representation of a distal end 1234 of the elongate device. Global view 1210 further displays the target location 1236 as determined from one or more anatomical models of the patient anatomy. As shown, the live current view 1232 of the elongate device along with the target location 1236 from the one or more anatomical models assists operator O in navigating the elongate device toward the target location 1236. Distance indicators 1238 show distance markers at distance increments of 1 cm, 2 cm, and 3 cm from the distal end 1234 of the elongate device.

Virtual view 1212 provides an orientation guide indicating the pose of the elongate device, as described herein. Coronal view 1214 acquired from the image data set includes a coronal image 1260 of the distal end of the elongate and a coronal image 1262 of the target location. Sagittal view 1216 acquired from the image data set includes a sagittal image 1264 of the distal end of the elongate and a sagittal image 1266 of the target location. Axial view 1218 acquired from the image data set includes an axial image 1268 of the distal end of the elongate and an axial image 1270 of the target location. Control system 112 can determine the positional and/or orientational differences in one or more degrees of freedom between the reference view 1230 of the elongate device and the current view 1232 of the elongate device and display information indicating those differences in information sidebar 1220.

Figure 13:
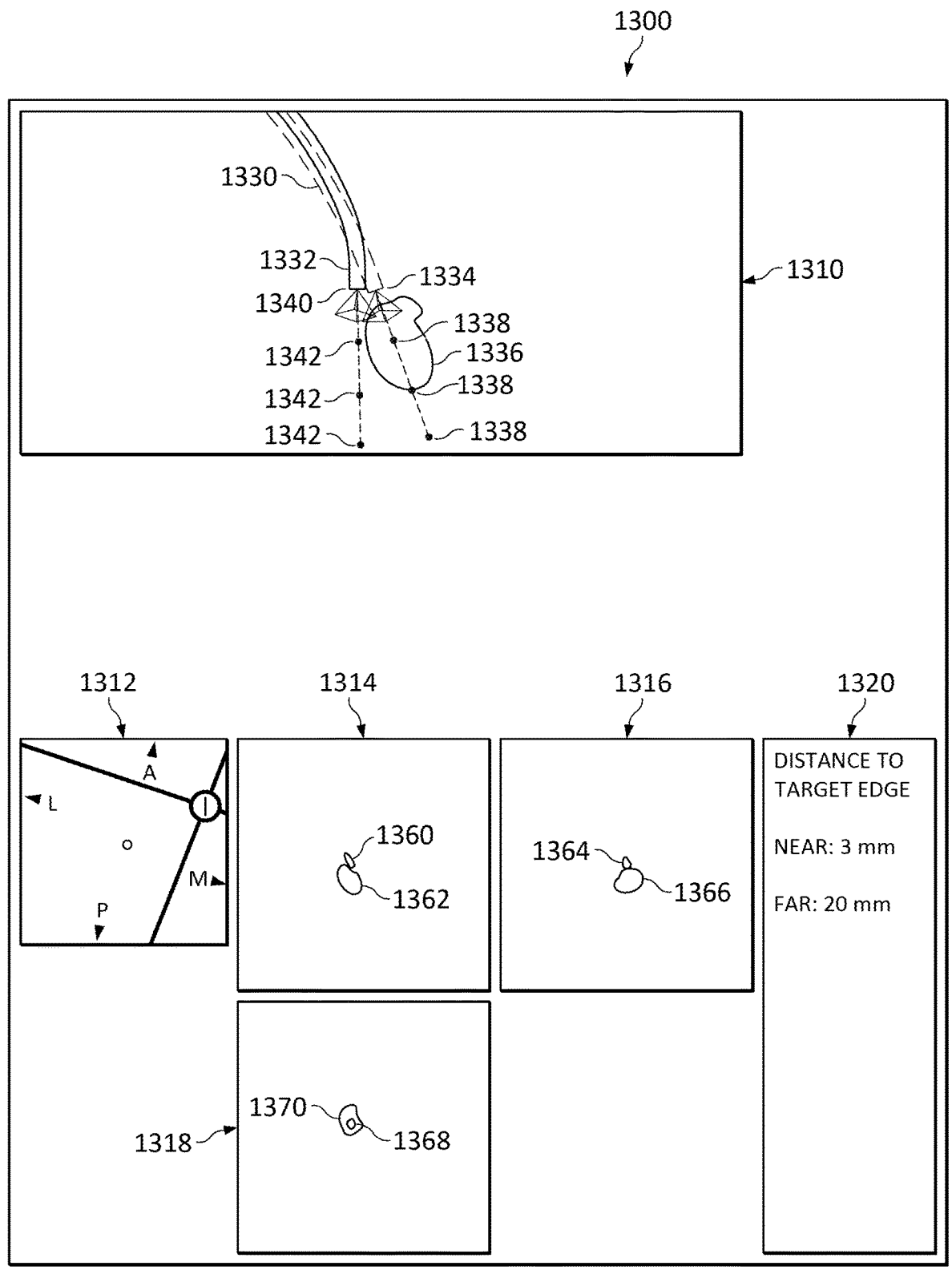
FIG. 13 illustrates a simplified diagram of a graphical user interface that includes a coronal view during articulation of an elongate device, according to some embodiments.

After viewing the elongated device in different views, the operator O selects a view, from which to articulate the elongate device to better position the elongate device relative to the target location. In the examples of FIGS. 10-13, the coronal view in global view 1010 provides the best perspective for indicating the best direction to articulate the elongate device in order to locate distal end in closer proximity to target location. FIG. 13 illustrates a simplified diagram of a graphical user interface that includes a coronal view during articulation of an elongate device, according to some embodiments. The graphical user interface 1300 includes, without limitation, a global view 1310 and a local view that further includes a virtual view 1312, a coronal view 1314, a sagittal view 1316, an axial view 1318, and an information sidebar 1320.

Global view 1310 displays a reference view 1330 with coronal perspective of the elongate device that represents a pose of the elongate device at a fixed point of time. Global view 1310 further displays a live current view 1332 with coronal perspective of the elongate device as the operator O articulates the elongate device along with distance indicators 1342. The operator O has articulated the elongate device such that the current location of the distal tip 1340 of the elongate device has moved relative to the reference location of the distal tip 1334 of the elongate device. The movement of the elongate device is further indicated by the change in location of the live view of distance indicators 1342 relative to the reference distance indicators 1338.

Virtual view 1312 provides an orientation guide indicating the pose of the elongate device, as described herein. Coronal view 1314 from the image data set includes a coronal image 1360 of the distal tip of the elongate and a coronal image 1362 of the target location. Sagittal view 1316 from the image data set includes a sagittal image 1364 of the distal tip of the elongate and a sagittal image 1366 of the target location. Axial view 1318 from the image data set includes an axial image 1368 of the distal end of the elongate and an axial image 1370 of the target location. Control system 112 can determine the positional and/or orientational differences in one or more degrees of freedom between the reference view 1330 of the elongate device and the current view 1332 of the elongate device and display information indicating those differences in information sidebar 1320.

Figure 14:
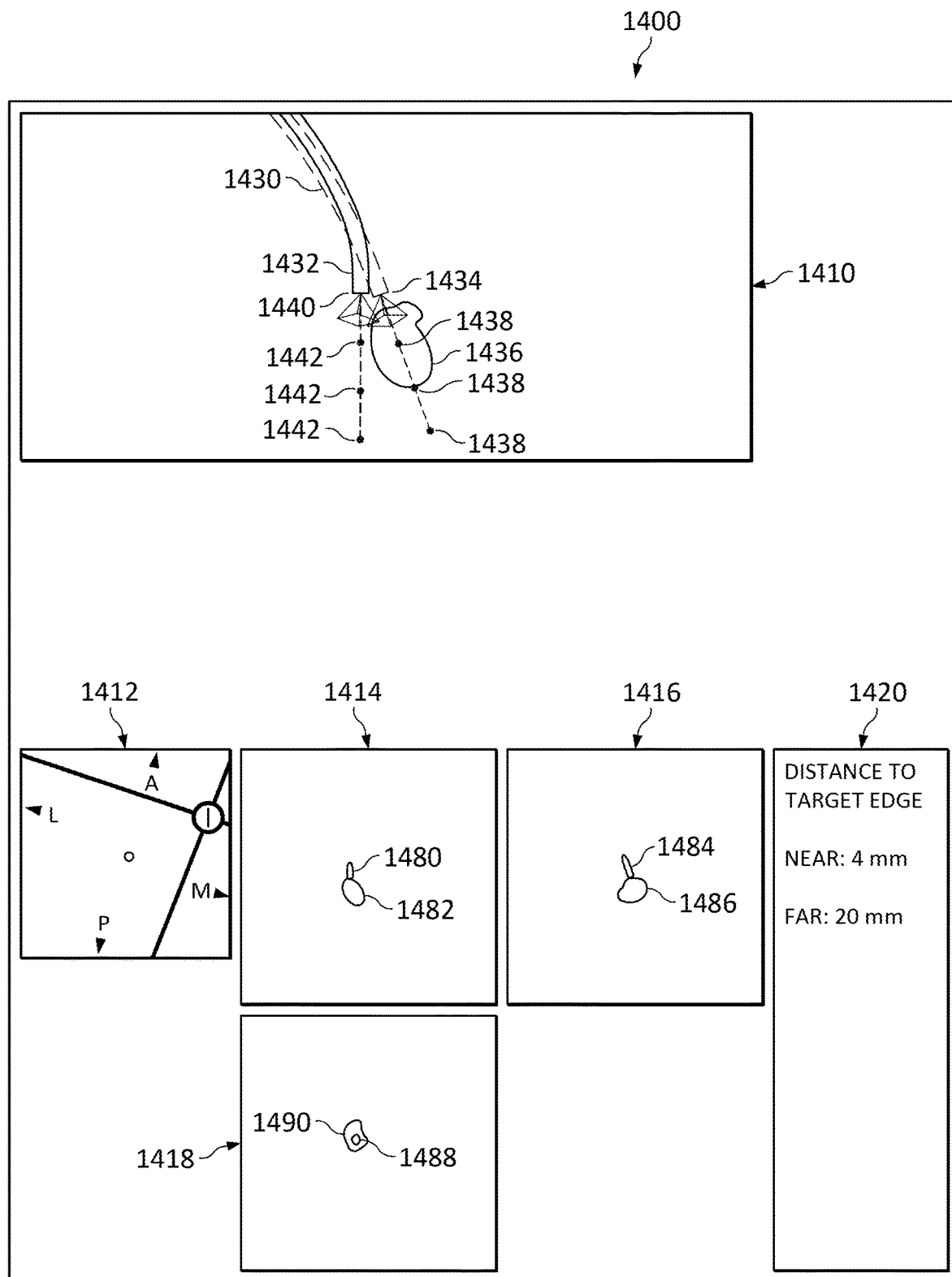
FIG. 14 illustrates a simplified diagram of a graphical user interface that includes a coronal view after articulation of an elongate device, according to some embodiments.

After articulating the elongate device to a new, desired pose, the operator O can acquire new images from a new intraoperative image data set of anatomic passageways based on the new pose. FIG. 14 illustrates a simplified diagram of a graphical user interface that includes a coronal view after articulation of an elongate device, according to some embodiments. The graphical user interface 1400 includes, without limitation, a global view 1410 and a local view that further includes a virtual view 1412, a coronal view 1414, a sagittal view 1416, an axial view 1418, and an information sidebar 1420.

Global view 1410 displays a reference view 1430 with coronal perspective of the elongate device that represents a pose of the elongate device at a fixed point of time. Global view 1410 further displays a live current view 1432 with coronal perspective of the elongate device as the operator O articulates the elongate device. The operator O has articulated the elongate device such that the current location of the distal end 1440 of the elongate device has moved relative to the reference location of the distal end 1434 of the elongate device. The movement of the elongate device is further indicated by the change in location of the live view of distance indicators 1442 relative to the reference distance indicators 1338.

Virtual view 1412 provides an orientation guide indicating the pose of the elongate device, as described herein. After the operator O has articulated the elongate device to the new pose, the operator O acquires new images from the preoperative or intraoperative image data set of anatomic passageways. Coronal view 1414, sagittal view 1416, and axial view 1418 are the new images acquired from the preoperative or intraoperative image data set of anatomic passageways. Coronal view 1414 is a new coronal view image acquired from the image data set. Coronal view 1414 includes a coronal image 1480 of the distal end of the elongate and a coronal image 1482 of the target location based on the new images. Sagittal view 1416 is a new sagittal view image acquired from the image data set. Sagittal view 1416 includes a sagittal image 1484 of the distal end of the elongate and a sagittal image 1486 of the target location based on the new images. Axial view 1418 is a new axial view image acquired from the image data set. Axial view 1418 includes an axial image 1488 of the distal end of the elongate and an axial image 1490 of the target location based on the new images. Control system 112 can determine the positional and/or orientational differences in one or more degrees of freedom between the reference view 1430 of the elongate device and the current view 1432 based on the new pose of the elongate device and display information indicating those differences in information sidebar 1420.

Figure 15:
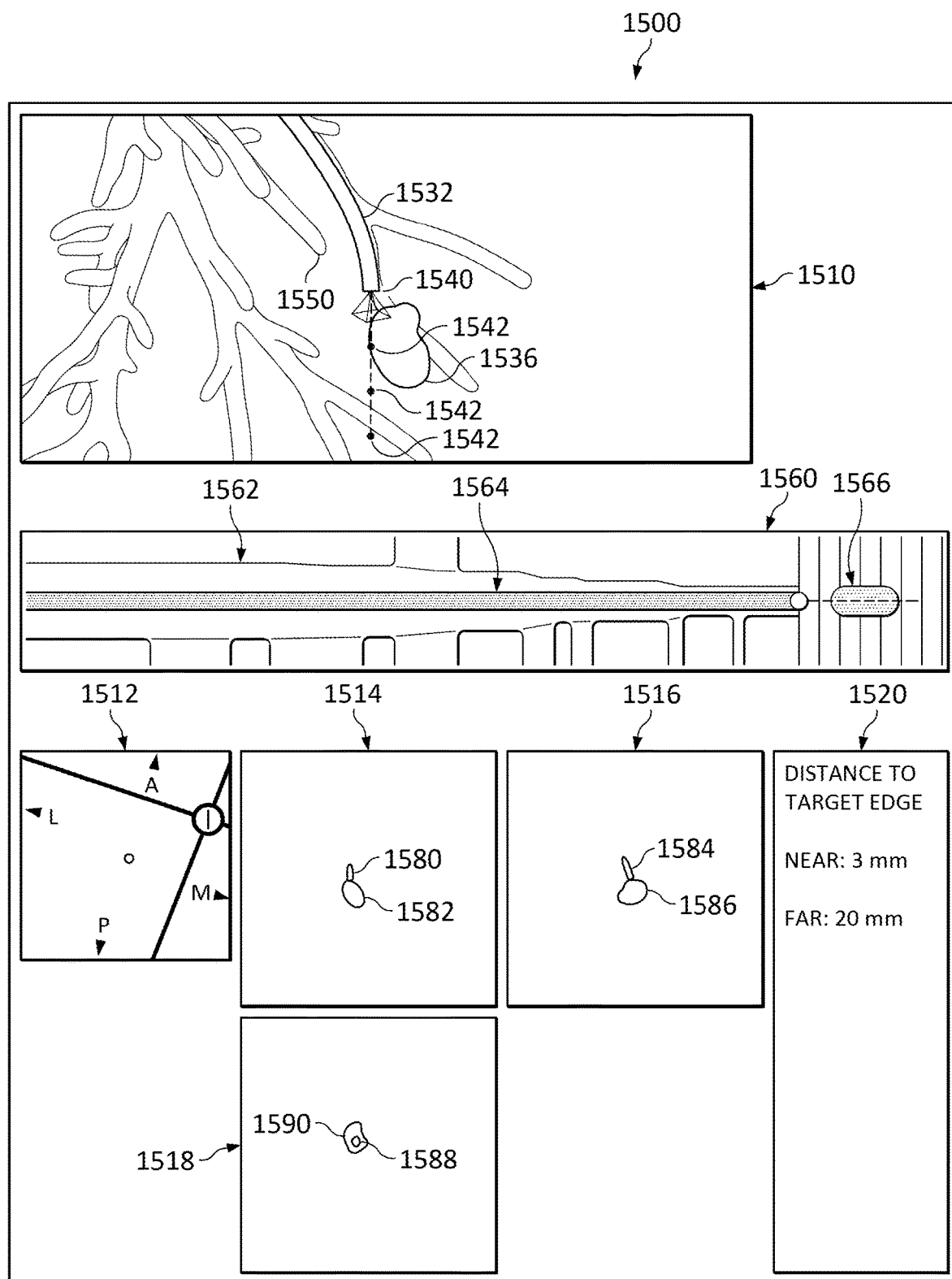
FIG. 15 is a simplified diagram of a user interface that includes a tree view and a navigation view of the elongate device, according to some embodiments.

After the operator O has articulated the elongate device to the new pose and has generated a new images acquired from the image data set based on the new pose, the operator O can switch the global view 1410 to show one or more other views generated from the 3D model of the patient anatomy and the current registration between the 3D model and the patient anatomy. In this manner, the operator O can view the elongate device located within the passageways of the patient anatomy of the 3D model and to determine how well the distal end of the elongate device is positioned relative to the target location. As indicated by the coronal image 1480 of the distal tip of the elongate and the coronal image 1482 of the target location in global view 1410, operator O has moved the distal end of the elongate device closer to the target location. FIG. 15 is a simplified diagram of a user interface that includes a tree view 1510 and a navigation view 1560 of the elongate device, according to some embodiments. The graphical user interface 1500 includes, without limitation, a tree view 1510, a navigation view 1560, and a local view that further includes a virtual view 1512, a coronal view 1514, a sagittal view 1516, an axial view 1518, and an information sidebar 1520.

Global view 1410 of FIG. 14 has been replaced by tree view 1510 and navigation view 1560 of the elongate device. Tree view 1510 and navigation view 1560 can be displayed as part of graphical user interface 1500 while operating in a navigation mode. Tree view 1510 includes a rendering 1550 of the 3D model with a depiction of the current view 1532 of the elongate device showing where the elongate device is located within the passageways of the patient anatomy of the 3D model. Tree view 1510 further includes a target location 1536, such as a target location within the passageways to which the elongate device is to be navigated. Tree view 1510 displays a representation of a distal end 1540 of the elongate device and further displays distance indicators 1542 that show distance markers at distance increments of 1 cm, 2 cm, and 3 cm from the distal end 1540 of the elongate device. Navigation view 1560 depicts widths and branching relationships of various anatomical passages along the length of navigation path 1562. Navigation view 1560 further shows a depiction 1564 of the progress of the elongate device along navigation path 1562 as the operator O navigates the elongate device towards the target location 1566.

Virtual view 1512 provides an orientation guide indicating the pose of the elongate device, as described herein. Coronal view 1514, sagittal view 1516, and axial view 1518 are images acquired from the image data set that were generated as described in conjunction with FIG. 14. Coronal view 1514 includes a coronal image 1580 of the distal end of the elongate and a coronal image 1582 of the target location. Sagittal view 1516 includes a sagittal image 1584 of the distal end of the elongate and a sagittal image 1586 of the target location. Axial view 1518 includes an axial image 1588 of the distal end of the elongate and an axial image 1590 of the target location. Control system 112 can determine the positional and/or orientational differences in one or more degrees of freedom between the reference view 1530 of the elongate device and the depiction of the current view 1532 based on the new pose of the elongate device and display information indicating those differences in information sidebar 1520.

Figure 16:
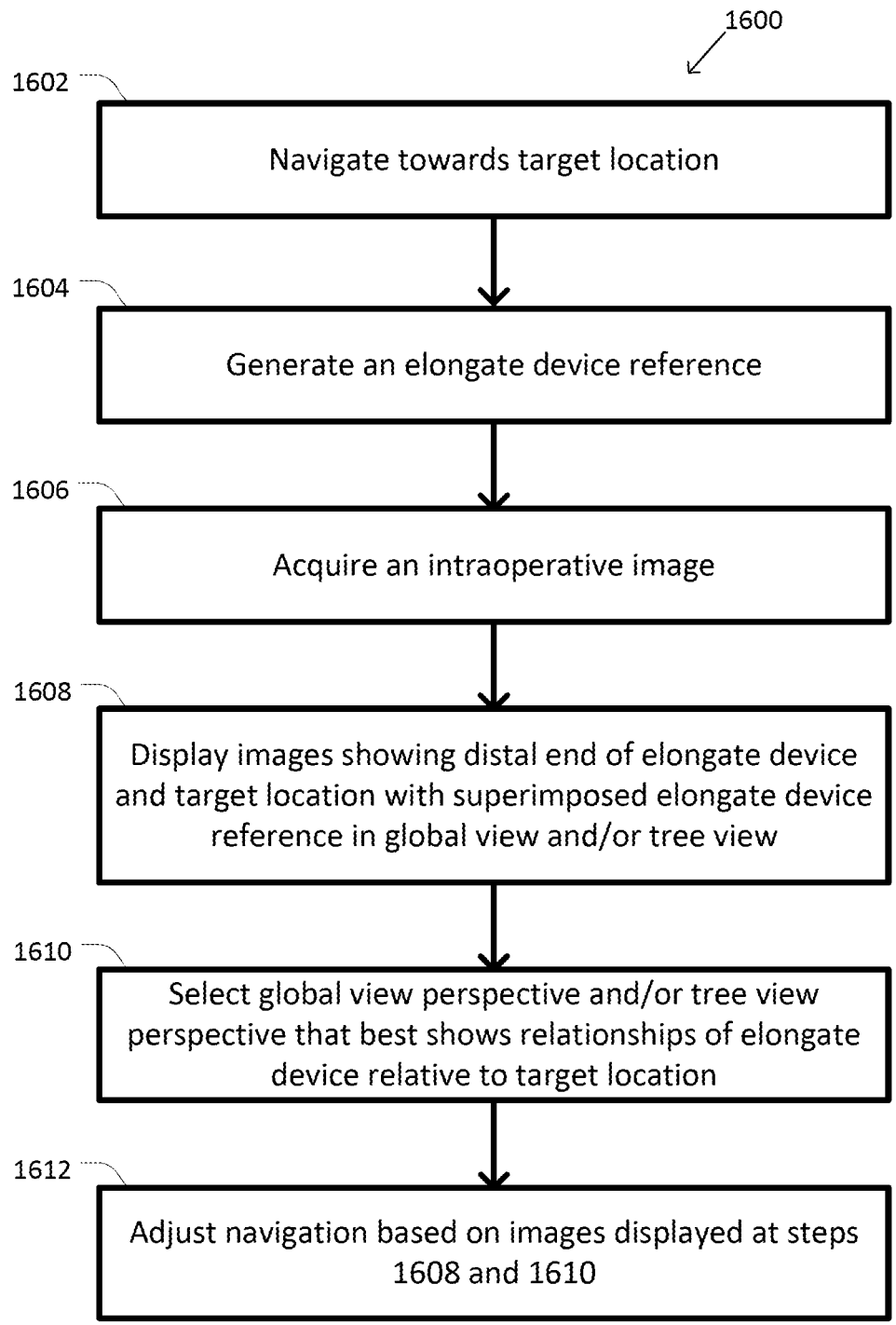
FIG. 16 is a flow chart of method steps for articulating an elongate device, according to some embodiments.

FIG. 16 is a flow chart of method steps for articulating an elongate device, according to some embodiments. Although the method steps are described with respect to the systems of FIGS. 1-8 and the user interfaces of 10-15, persons skilled in the art will understand that any system configured to perform the method steps, in any order, falls within the scope of the various embodiments. In some embodiments, one or more of the steps 1602-1612 of method 1600 may be implemented, at least in part, in the form of executable code stored on one or more non-transient, tangible, machine readable media that when run by one or more processors (e.g., one or more processors of control system 112) would cause the one or more processors to perform one or more of the steps 1602-1610.

As shown, method 1600 begins at step 1602, where operator O navigates the elongate device towards a target location. Control system 112 updates a graphic user interface as Operator O navigates the elongate device to the target location. Operator O inserts minimally invasive medical instruments (including surgical, diagnostic, therapeutic, or biopsy instruments) through natural orifices in a patient anatomy or through one or more surgical incisions to reach a target tissue location. In some examples, operator O inserts a flexible and/or steerable elongate device, such as a catheter, into anatomic passageways and navigates the steerable elongate device toward a region of interest within the patient anatomy. Control system 112 determines a current pose (e.g., current position and/or orientation) of the elongate device (e.g., within a passageway in the patient anatomy of patient P). Control system 112 determines the pose of the elongate device by, for example, obtaining data from sensor system 108.

At step 1604, control system 112 generates an elongate device reference corresponding to the reference pose. The control system 112 can acquire a reference pose of the elongate device, including the distal end of the elongate device. In some examples, control system 112 loads a reference pose of the elongate device from a pre-operative plan or from a pose previously recorded during the current procedure or a prior procedure. In some instances, the reference pose may be the pose of the elongate device determined in step 1602. The reference pose can be acquired in response to a command of operator O to, for example, save the reference pose.

At step 1606, control system 112 acquires intraoperative images of the elongate device. For example, the intraoperative images can be obtained via CBCT. Control system 112 determines a current pose (e.g., current position and/or orientation) of the elongate device (e.g., within a passageway in the patient anatomy of patient P) as the operator O articulates the elongate device. Control system 112 determines the pose of the elongate device, for example, obtaining data from sensor system 108.

At step 1608, control system 112 displays images showing the distal end of the elongate device and target location with superimposed elongate device reference in global view and/or tree view. Control system 112 can generate a 3D object that is a stylized representation or a virtual duplicate of the elongate device in the reference pose (e.g., reference view 1030, 1130, 1230). The 3D object can be displayed at a position and orientation corresponding to the reference pose on a global view and/or a local view of a graphical user interface. Further, control system 112 generates an elongate device live view corresponding to the current pose. Control system 112 can generate a 3D object that is a stylized representation or a virtual duplicate of the elongate device in the current pose (e.g., live current view 1032, 1132, 1232). The 3D object can be displayed at a position and orientation corresponding to the current pose on a global view and/or a local view of a graphical user interface. The elongate device in the reference pose and in the current pose can be displayed in various views, including one or more of a coronal view (e.g., global view 1010), an axial view (e.g., global view 1110), a sagittal view (e.g., global view 1210), a tree view, and a navigation view (e.g., navigation view 1560). In this manner, the operator O is able use the graphical user interface to simultaneously view the elongate device in the reference pose and the elongate device in the current pose.

At step 1610, control system 112 selects a global view perspective and/or tree view perspective that best shows relationships of the reference pose and the current pose of the elongate device relative to the target location. Control system 112 selects the global view and/or tree view perspective in response to a command of operator O to, for example, change the current view of the graphical user interface. In that regard, the operator O can generate a command to change the current view to include a coronal view of the elongate device in the reference pose and the elongate device in the current pose (e.g., global view 1010). Alternatively, the operator O can generate a command to change the current view to include an axial view of the elongate device in the reference pose and the elongate device in the current pose (e.g., global view 1110). Alternatively, the operator O can generate a command to change the current view to include a sagittal view of the elongate device in the reference pose and the elongate device in the current pose (e.g., global view 1210).

Further, the operator O can generate a command to change the current view to include a tree view and/or a navigation view. The tree view includes a rendering of the 3D model with a depiction of the elongate device showing where the elongate device is located within the passageways of the patient anatomy of the 3D model (e.g., tree view 1510). The navigation view further shows a depiction of the progress of the elongate device along navigation path as the operator O navigates the elongate device towards the target location (e.g., navigation view 1560). Depending on the reference pose and the current pose, the operator O which of the coronal view, axial view, sagittal view, tree view, and/or navigation provides the best view of the reference pose and the current pose of the elongate device relative to the target location.

At step 1612, control system 112 adjusts the navigation based on images displayed on the graphical user interface at one or both of steps 1608 and 1610. Control system 112 adjusts the navigation in response to a command of operator O to, for example, articulate the distal end of the elongate device to a desired pose as shown on the current view of the graphical user interface. As an example, the movement of the elongate device from the pose shown in FIGS. 10-12 relative to the pose shown in FIGS. 15 and 16 shows the effects of such an articulation.

In some embodiments, one or more of the steps of method 1600 can be repeated as needed to display the elongate device at another reference pose and/or another current pose. For example, after adjusting the navigation in step 1612, the method can proceed to step 1604 to generate another elongate device reference. In some embodiments, multiple elongate device references corresponding to different reference poses can be displayed concurrently along with a representation (virtual representation or image capture) of the elongate device corresponding to the current pose.

In sum, a technique provides an elongate device reference during an image-guided procedure. A computing system determines a pose of an elongate device (e.g., an instrument, such as a catheter) and/or an instrument extending from the elongate device within a workspace (e.g., passageway within a patient anatomy). The computing device can acquire a reference pose from a pre-operative plan and/or data recorded during a procedure. The computing system generates an elongate device reference associated with the reference pose. The computing system displays a live camera view and/or a virtual view from a perspective associated with the elongate device, and concurrently displays the elongate device reference at the reference pose on the live camera view and/or the virtual view. The computing system can further display metadata associated with the reference pose, and navigational difference information between the reference pose and the current pose, concurrently with the elongate device reference.

At least one advantage and technical improvement of the disclosed techniques relative to the prior art is that, with the disclosed techniques, planned and/or saved poses of an elongate device can be shown in three dimensions and/or in multiple degrees of freedom in images of a workspace of interest. Accordingly, an operator of the elongate device can more effectively navigate the elongate device within the workspace to a planned or saved pose. Another advantage and technical improvement is that points of interest can be associated with saved and/or planned poses in 3D and/or in multiple degrees of freedom. Accordingly, the operator can more effectively navigate the elongate device within the workspace to those points of interest. These technical advantages provide one or more technological advancements over prior art approaches.

1. In some embodiments, a system comprises: an elongate device; a display system; one or more processors; and memory storing instructions that, when executed by the one or more processors, cause the one or more processors to: determine a pose, within a workspace, of at least one of: a distal portion of the elongate device, or an instrument extendable from the distal portion of the elongate device; acquire a reference pose of the at least one of: the distal portion of the elongate device, or the instrument; generate an elongate device reference corresponding to the reference pose; generate an image of the workspace from a perspective associated with the pose; and display, on the display system and on the image of the workspace, the elongate device reference at the reference pose.
2. The system according to clause 1, wherein the pose comprises at least one of: a position and an orientation of the distal portion of the elongate device within the workspace, or a position and an orientation of the instrument relative to the workspace.
3. The system according to clause 1 or clause 2, wherein the image of the workspace corresponds to a first-person view associated with the pose.
4. The system according to any of clauses 1-3, wherein the image of the workspace corresponds to a third-person view associated with the pose.
5. The system according to any of clauses 1-4, wherein the elongate device reference comprises a stylized representation of the elongate device.
6. The system according to any of clauses 1-5, wherein the elongate device reference comprises a virtual duplicate of the elongate device.
7. The system according to any of clauses 1-6, wherein the elongate device reference comprises an orientation pointer indicating an orientation of the at least one of the distal portion of the elongate device or the instrument.
8. The system according to any of clauses 1-7, wherein the orientation pointer indicates a reach of the instrument when the instrument is extended from the distal portion of the elongate device.
9. The system according to any of clauses 1-8, wherein the elongate device reference comprises a length reference associated with at least one of the elongate device or the instrument.
10. The system according to any of clauses 1-9, wherein the length reference comprises markers of predefined length increments.
11. The system according to any of clauses 1-10, wherein the elongate device reference is associated with a point of interest in the workspace.
12. The system according to any of clauses 1-11, wherein the memory stores instructions that, when executed by the one or more processors, further cause the one or more processors to: generate a virtual representation of the elongate device corresponding to the pose; and display, on the display system and on the image of the workspace, the virtual representation of the elongate device at the pose.
13. The system according to any of clauses 1-12, wherein the virtual representation of the elongate device is displayed on the image of the workspace concurrently with the elongate device reference.
14. The system according to any of clauses 1-12, wherein the instructions that, when executed by the one or more processors, further cause the one or more processors to: acquire a second reference pose of the at least one of the distal portion of the elongate device or the instrument; generate a second elongate device reference corresponding to the second reference pose; and display, on the display system and on the image of the workspace, the second elongate device reference at the second reference pose.
15. The system according to any of clauses 1-14, wherein the second elongate device reference is displayed on the image of the workspace concurrently with the elongate device reference.
16. The system according to any of clauses 1-15, wherein the second elongate device reference is visually distinct from the elongate device reference by at least one of color, shading, or labeling.
17. The system according to any of clauses 1-16, wherein each of the elongate device reference and the second elongate device reference is selectable by an operator.
18. The system according to any of clauses 1-17, wherein the instructions that, when executed by the one or more processors, further cause the one or more processors to display, on the display system, metadata associated with the reference pose concurrently with the elongate device reference.
19. The system according to any of clauses 1-18, wherein the metadata associated with the reference pose comprises one or more of an identifier of the reference pose, a timestamp of the reference pose, an operator associated with the reference pose, an instrument associated with the reference pose, or a description of the reference pose.
20. The system according to any of clauses 1-19, wherein the metadata associated with the reference pose comprises navigational information corresponding to a difference between the reference pose and the pose.
21. The system according to any of clauses 1-20, wherein the reference pose is acquired from one or more of a pre-operative plan, a record of a previously performed procedure, or a record of a current procedure.
22. In some embodiments, an apparatus comprises: one or more processors; and memory storing instructions that, when executed by the one or more processors, cause the one or more processors to: determine a pose, within a workspace, of a distal portion of at least one of an elongate device or an instrument extended beyond the distal portion of the elongate device; acquire a reference pose of the distal portion of at least one of the elongate device or the instrument; generate an elongate device reference corresponding to the reference pose; generate an image of the workspace from a perspective associated with the pose; and output, for display on a display system, the elongate device reference at the reference pose in the image.
23. The apparatus according to clause 22, wherein the pose comprises at least one of: a position and an orientation of the distal portion of the elongate device within the workspace, or a position and an orientation of the instrument relative to the workspace.
24. The apparatus according to clause 22 or clause 23, wherein the image of the workspace corresponds to a first-person view associated with the pose.
25. The apparatus according to any of clauses 22-24, wherein the image of the workspace corresponds to a third-person view associated with the pose.
26. The apparatus according to any of clauses 22-25, wherein the elongate device reference comprises a stylized representation of the elongate device.

27. The apparatus according to any of clauses 22-26, wherein the elongate device reference comprises a virtual duplicate of the elongate device.
28. The apparatus according to any of clauses 22-27, wherein the elongate device reference comprises an orientation pointer indicating an orientation of the at least one of the distal portion of the elongate device or the instrument.
29. The apparatus according to any of clauses 22-28, wherein the orientation pointer indicates a reach of the instrument when the instrument is extended from the distal portion of the elongate device.
30. The apparatus according to any of clauses 22-29, wherein the elongate device reference comprises a length reference associated with at least one of the elongate device or the instrument.
31. The apparatus according to any of clauses 22-30, wherein the length reference comprises markers of predefined length increments.
32. The apparatus according to any of clauses 22-31, wherein the elongate device reference is associated with a point of interest in the workspace.
33. The apparatus according to any of clauses 22-32, wherein the instructions that, when executed by the one or more processors, further cause the one or more processors to: generate a virtual representation of the elongate device corresponding to the pose; and output, for display on the display system and on the image of the workspace, the virtual representation of the elongate device at the pose.
34. The apparatus according to any of clauses 22-33, wherein the virtual representation of the elongate device is displayed on the image of the workspace concurrently with the elongate device reference.
35. The apparatus according to any of clauses 22-34, wherein the instructions that, when executed by the one or more processors, further cause the one or more processors to: acquire a second reference pose of the at least one of the distal portion of the elongate device or the instrument; generate a second elongate device reference corresponding to the second reference pose; and output, for display on the display system and on the image of the workspace, the second elongate device reference at the second reference pose.
36. The apparatus according to any of clauses 22-35, wherein the second elongate device reference is displayed on the image of the workspace concurrently with the elongate device reference.
37. The apparatus according to any of clauses 22-36, wherein the second elongate device reference is visually distinct from the elongate device reference by at least one of color, shading, or labeling.
38. The apparatus according to any of clauses 22-37, wherein each of the elongate device reference and the second elongate device reference is selectable by an operator.
39. The apparatus according to any of clauses 22-38, wherein the instructions that, when executed by the one or more processors, further cause the one or more processors to output, for display on the display system, metadata associated with the reference pose, wherein the metadata is displayed concurrently with the elongate device reference.
40. The apparatus according to any of clauses 22-39, wherein the metadata associated with the reference pose comprises one or more of an identifier of the reference pose, a timestamp of the reference pose, an operator associated with the reference pose, an instrument associated with the reference pose, or a description of the reference pose.
41. The apparatus according to any of clauses 22-40, wherein the metadata associated with the reference pose comprises navigational information corresponding to a difference between the reference pose and the pose.
42. The apparatus according to any of clauses 22-41, wherein the reference pose is acquired from one or more of a pre-operative plan, a record of a previously performed procedure, or a record of a current procedure.
43. In some embodiments, a method comprises: determining a pose, within a workspace, of at least one of: a distal portion of an elongate device, or an instrument extendable from the distal portion of the elongate device; acquiring a reference pose of the at least one of: the distal portion of the elongate device, or the instrument; generating an elongate device reference corresponding to the reference pose; generating an image of the workspace from a perspective associated with the pose; and causing to be displayed, on a display system and on the image of the workspace, the elongate device reference at the reference pose.
44. The method according to clause 43, wherein the pose comprises at least one of: a position and an orientation of the distal portion of the elongate device within the workspace, or a position and an orientation of the instrument relative to the workspace.
45. The method according to clause 43 or clause 44, wherein the image of the workspace corresponds to a first-person view associated with the pose.
46. The method according to any of clauses 43-45, wherein the image of the workspace corresponds to a third-person view associated with the pose.
47. The method according to any of clauses 43-46, wherein the elongate device reference comprises a stylized representation of the elongate device.
48. The method according to any of clauses 43-47, wherein the elongate device reference comprises a virtual duplicate of the elongate device.
49. The method according to any of clauses 43-48, wherein the elongate device reference comprises an orientation pointer indicating an orientation of the at least one of the distal portion of the elongate device or the instrument.
50. The method according to any of clauses 43-49, wherein the orientation pointer indicates a reach of the instrument when the instrument is extended from the distal portion of the elongate device.
51. The method according to any of clauses 43-50, wherein the elongate device reference comprises a length reference associated with at least one of the elongate device or the instrument.
52. The method according to any of clauses 43-51, wherein the length reference comprises markers of predefined length increments.
53. The method according to any of clauses 43-52, wherein the elongate device reference is associated with a point of interest in the workspace.
54. The method according to any of clauses 43-53, further comprising: generating a virtual representation of the elongate device corresponding to the pose; and causing to be displayed, on the display system and on the image of the workspace, the virtual representation of the elongate device at the pose.

55. The method according to any of clauses 43-54, wherein the virtual representation of the elongate device is displayed on the image of the workspace concurrently with the elongate device reference.
56. The method according to any of clauses 43-55, further comprising: acquiring a second reference pose of the at least one of the distal portion of the elongate device or the instrument; generating a second elongate device reference corresponding to the second reference pose; and causing to be displayed, on the display system and on the image of the workspace, the second elongate device reference at the second reference pose.
57. The method according to any of clauses 43-56, wherein the second elongate device reference is displayed on the image of the workspace concurrently with the elongate device reference.
58. The method according to any of clauses 43-57, wherein the second elongate device reference is visually distinct from the elongate device reference by at least one of color, shading, or labeling.
59. The method according to any of clauses 43-58, wherein each of the elongate device reference and the second elongate device reference is selectable by an operator.
60. The method according to any of clauses 43-59, further comprising causing to be displayed, on the display system, metadata associated with the reference pose concurrently with the elongate device reference.
61. The method according to any of clauses 43-60, wherein the metadata associated with the reference pose comprises one or more of an identifier of the reference pose, a timestamp of the reference pose, an operator associated with the reference pose, an instrument associated with the reference pose, or a description of the reference pose.
62. The method according to any of clauses 43-61, wherein the metadata associated with the reference pose comprises navigational information corresponding to a difference between the reference pose and the pose.
63. The method according to any of clauses 43-62, wherein the reference pose is acquired from one or more of a pre-operative plan, a record of a previously performed procedure, or a record of a current procedure.
64. In some embodiments, one or more non-transitory machine-readable media comprise a plurality of machine-readable instructions which when executed by one or more processors are adapted to cause the one or more processors to perform the method of any one of claims 43-63.
65. In some embodiments, a system comprises: an elongate device; a display system; one or more processors; and memory storing instructions that, when executed by the one or more processors, cause the one or more processors to: determine a current pose, within a workspace, of an elongate device; acquire a reference pose of the elongate device; generate an elongate device reference corresponding to the reference pose; generate an image of the elongate device reference; generate an image of the elongate device at the current pose; display, on the display system, the image of the elongate device reference at the reference pose; and display, on the display system, the image of the elongate device at the current pose.
66. The system according to clause 65, wherein the current pose comprises a position and an orientation of the elongate device within the workspace.
67. The system according to clause 65 or clause 66, wherein the instructions that, when executed by the one or more processors, further cause the one or more processors to receive a selection of a view perspective associated with the elongate device, wherein the image of the elongate device reference and the image of the elongate device at the current pose are generated from the view perspective.
68. The system according to any of clauses 65-67, wherein the view perspective includes at least one of a coronal view, an axial view, or a sagittal view.
69. The system according to any of clauses 65-68, wherein the instructions that, when executed by the one or more processors, further cause the one or more processors to display, on the display system, an image of a target location.
70. The system according to any of clauses 65-69, wherein the instructions that, when executed by the one or more processors, further cause the one or more processors to: acquire a set of images from an intraoperative image data set of anatomic passageways included in the workspace based on the reference pose; and display, on the display system, the set of images.
71. The system according to any of clauses 65-70, wherein the set of images includes at least one of a coronal view, an axial view, or a sagittal view.
72. The system according to any of clauses 65-71, wherein each image in set of images depicts a distal end of the elongate device and a target location.
73. The system according to any of clauses 65-72, wherein the instructions, when executed by the one or more processors, further cause the one or more processors to display, on the display system, a set of distance markers that indicate distance increments from a distal end of the elongate device.

Any and all combinations of any of the claim elements recited in any of the claims and/or any elements described in this application, in any fashion, fall within the contemplated scope of the present disclosure and protection.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "module," a "system," or a "computer." In addition, any hardware and/or software technique, process, function, component, engine, module, or system described in the present disclosure may be implemented as a circuit or set of circuits. Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RANI), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine. The instructions, when executed via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A system, comprising:
   an elongate device;
   a display system;
   one or more processors; and
   memory storing instructions that, when executed by the one or more processors, cause the one or more processors to:
      determine a pose, within a workspace, of at least one of:
         a distal portion of the elongate device, or
         an instrument extendable from the distal portion of the elongate device;
      acquire a reference pose of the at least one of:
         the distal portion of the elongate device, or
         the instrument;
      generate an elongate device reference corresponding to the reference pose;
      generate an image of the workspace from a perspective of a point located behind the distal portion of the elongate device; and
      display, on the display system and on the image of the workspace, the elongate device reference at the reference pose and the distal portion of the elongate device.

2. The system of claim 1, wherein the pose comprises at least one of:
   a position and an orientation of the distal portion of the elongate device within the workspace, or
   a position and an orientation of the instrument relative to the workspace.

3. The system of claim 1, wherein the image of the workspace corresponds to a first-person view associated with the pose or a third-person view associated with the pose.

4. The system of claim 1, wherein the elongate device reference comprises a stylized representation of the elongate device or a virtual duplicate of the elongate device.

5. The system of claim 1, wherein the elongate device reference comprises an orientation pointer indicating an orientation of the at least one of the distal portion of the elongate device or the instrument.

6. The system of claim 5, wherein the orientation pointer indicates a reach of the instrument when the instrument is extended from the distal portion of the elongate device.

7. The system of claim 1, wherein the elongate device reference is associated with a point of interest in the workspace.

8. The system of claim 1, wherein the memory stores instructions that, when executed by the one or more processors, further cause the one or more processors to:
   generate a virtual representation of the elongate device corresponding to the pose; and
   display, on the display system and on the image of the workspace, the virtual representation of the elongate device at the pose.

9. The system of claim 8, wherein the virtual representation of the elongate device is displayed on the image of the workspace concurrently with the elongate device reference.

10. The system of claim 1, wherein the instructions that, when executed by the one or more processors, further cause the one or more processors to:
    acquire a second reference pose of the at least one of the distal portion of the elongate device or the instrument;
    generate a second elongate device reference corresponding to the second reference pose; and
    display, on the display system and on the image of the workspace, the second elongate device reference at the second reference pose.

11. The system of claim 1, wherein the instructions that, when executed by the one or more processors, further cause the one or more processors to display, on the display system, metadata associated with the reference pose concurrently with the elongate device reference.

12. A method, comprising:
  determining a pose, within a workspace, of at least one of:
    a distal portion of an elongate device, or
    an instrument extendable from the distal portion of the elongate device;
  acquiring a reference pose of:
    the distal portion of the elongate device, or
    the instrument;
  generating an elongate device reference corresponding to the reference pose;
    generating an image of the workspace from a perspective of a point located behind the distal portion of the elongate device; and
  causing to be displayed, on a display system and on the image of the workspace, the elongate device reference at the reference pose and the distal portion of the elongate device.

13. The method of claim 12, wherein the pose comprises at least one of:
  a position and an orientation of the distal portion of the elongate device within the workspace, or
  a position and an orientation of the instrument relative to the workspace.

14. The method of claim 12, wherein the image of the workspace corresponds to a first-person view associated with the pose or a third-person view associated with the pose.

15. The method of claim 12, wherein the elongate device reference comprises a stylized representation of the elongate device or a virtual duplicate of the elongate device.

16. The method of claim 12, wherein the elongate device reference comprises an orientation pointer indicating an orientation of the at least one of the distal portion of the elongate device or the instrument.

17. The method of claim 12, further comprising:
  generating a virtual representation of the elongate device corresponding to the pose; and
  causing to be displayed, on the display system and on the image of the workspace, the virtual representation of the elongate device at the pose.

18. One or more non-transitory machine-readable media comprising a plurality of machine-readable instructions which when executed by one or more processors are adapted to cause the one or more processors to perform a method comprising:
  determining a pose, within a workspace, of at least one of:
    a distal portion of an elongate device, or
    an instrument extendable from the distal portion of the elongate device;
  acquiring a reference pose of:
    the distal portion of the elongate device, or
    the instrument;
  generating an elongate device reference corresponding to the reference pose;
  generating an image of the workspace from a perspective of a point located behind the distal portion of the elongate device; and
  causing to be displayed, on a display system and on the image of the workspace, the elongate device reference at the reference pose and the distal portion of the elongate device.

19. The one or more non-transitory machine-readable media of claim 18, wherein the pose comprises at least one of:
  a position and an orientation of the distal portion of the elongate device within the workspace, or
  a position and an orientation of the instrument relative to the workspace.

20. The one or more non-transitory machine-readable media of claim 18, wherein the image of the workspace corresponds to a first-person view associated with the pose or a third-person view associated with the pose.

* * * * *